United States Patent
Qiu

(10) Patent No.: US 12,365,734 B2
(45) Date of Patent: Jul. 22, 2025

(54) ANTI-ALPHA BETA TCR BINDING POLYPEPTIDES WITH REDUCED FRAGMENTATION

(71) Applicant: Genzyme Corporation, Cambridge, MA (US)

(72) Inventor: Huawei Qiu, Bridgewater, NJ (US)

(73) Assignee: GENZYME CORPORATION, Cambridge, MA (US)

(*) Notice: Subject to any disclaimer, the term of this patent is extended or adjusted under 35 U.S.C. 154(b) by 877 days.

(21) Appl. No.: 17/441,028

(22) PCT Filed: Apr. 2, 2020

(86) PCT No.: PCT/US2020/026304
§ 371 (c)(1),
(2) Date: Sep. 20, 2021

(87) PCT Pub. No.: WO2020/206063
PCT Pub. Date: Oct. 8, 2020

(65) Prior Publication Data
US 2022/0153840 A1    May 19, 2022

Related U.S. Application Data

(60) Provisional application No. 62/828,601, filed on Apr. 3, 2019.

(51) Int. Cl.
*C07K 16/28* (2006.01)

(52) U.S. Cl.
CPC ...... *C07K 16/2809* (2013.01); *C07K 2317/24* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. |
| 4,816,397 A | 3/1989 | Boss et al. |
| 4,816,567 A | 3/1989 | Cabilly et al. |
| 5,108,921 A | 4/1992 | Low et al. |
| 5,149,782 A | 9/1992 | Chang et al. |
| 5,225,539 A | 7/1993 | Winter |
| 5,314,995 A | 5/1994 | Fell, Jr. et al. |
| 5,429,746 A | 7/1995 | Shadle et al. |
| 5,606,017 A | 2/1997 | Willner et al. |
| 5,648,260 A | 7/1997 | Winter et al. |
| 5,739,277 A | 4/1998 | Presta et al. |
| 5,792,456 A | 8/1998 | Yelton et al. |
| 5,834,250 A | 11/1998 | Wells et al. |
| 5,837,821 A | 11/1998 | Wu |
| 5,869,046 A | 2/1999 | Presta et al. |
| 5,880,270 A | 3/1999 | Berninger et al. |
| 5,989,830 A | 11/1999 | Davis et al. |
| 6,096,871 A | 8/2000 | Presta et al. |
| 6,121,022 A | 9/2000 | Presta et al. |
| 6,193,980 B1 | 2/2001 | Efstathiou et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |
| 6,277,375 B1 | 8/2001 | Ward |
| 6,465,612 B1 | 10/2002 | Bertozzi et al. |
| 6,514,498 B1 | 2/2003 | Antonsson et al. |
| 6,528,624 B1 | 3/2003 | Idusogie et al. |
| 6,538,124 B1 | 3/2003 | Idusogie et al. |
| 6,737,056 B1 | 5/2004 | Presta |
| 6,821,505 B2 | 11/2004 | Ward |
| 6,998,253 B1 | 2/2006 | Presta et al. |
| 7,083,784 B2 | 8/2006 | Dall'Acqua et al. |
| 7,183,387 B1 | 2/2007 | Presta |
| 7,317,091 B2 | 1/2008 | Lazar et al. |
| 7,332,581 B2 | 2/2008 | Presta |
| 7,335,742 B2 | 2/2008 | Presta |
| 7,338,933 B2 | 3/2008 | Defrees et al. |

(Continued)

FOREIGN PATENT DOCUMENTS

| | | |
|---|---|---|
| CN | 1255378 A | 6/2000 |
| CN | 1867583 A | 11/2006 |

(Continued)

OTHER PUBLICATIONS

MacCallum et al. (1996). J. Mol. Biol. 262:732-745.*
De Pascalis et al. (2002). Journal of Immunology. 169:3076-3084.*
Haberger et al., "Assessment of chemical modifications of sites in the CDRs of recombinant antibodies", MAbs, Mar./Apr. 2014, vol. 6, No. 2, pp. 327-339.
International Search Report and Written Opinion received for PCT Patent Application No. PCT/US2020/026304, mailed on Jul. 20, 2020.
Lu et al., "Deamidation and isomerization liability analysis of 131 clinical-stage antibodies", MAbs, Jan. 2019, vol. 11, No. 1, pp. 45-57.

(Continued)

*Primary Examiner* — Christine J Saoud
*Assistant Examiner* — Jon M Lockard
(74) *Attorney, Agent, or Firm* — LATHROP GPM LLP; James H. Velema, Esq.

(57) ABSTRACT

The present disclosure is related to improved compositions and methods for treating T-cell-mediated diseases and disorders (e.g., autoimmune disorders, graft-versus-host-disease, and graft rejection). Provided are anti-apβTCR binding polypeptides, including antibodies, which comprise at least one amino acid substitution or modification that increases the stability of the binding polypeptide by reducing fragmentation of the light chain variable region. The methods provided herein generally involve administering to a subject in need thereof an effective amount of a stabilized, humanized binding polypeptide that is specific to the alpha beta T-cell receptor (apβTCR).

21 Claims, 13 Drawing Sheets

Specification includes a Sequence Listing.

(56) References Cited

U.S. PATENT DOCUMENTS

| | | |
|---|---|---|
| 7,355,008 B2 | 4/2008 | Stavenhagen et al. |
| 7,371,826 B2 | 5/2008 | Presta |
| 7,612,181 B2 | 11/2009 | Wu et al. |
| 7,785,791 B2 | 8/2010 | Presta |
| 7,790,858 B2 | 9/2010 | Presta |
| 8,163,881 B2 | 4/2012 | Ober |
| 8,361,961 B2 | 1/2013 | Defrees et al. |
| 9,187,532 B2 | 11/2015 | Defrees |
| 9,580,511 B2 | 2/2017 | Pan et al. |
| 9,701,753 B2 | 7/2017 | Pan et al. |
| 9,790,268 B2 | 10/2017 | Pan et al. |
| 10,017,573 B2 | 7/2018 | Snell et al. |
| 10,064,952 B2 | 9/2018 | Avila et al. |
| 10,214,589 B2 | 2/2019 | Pan et al. |
| 10,494,439 B2 | 12/2019 | Pan et al. |
| 10,995,148 B2 | 5/2021 | Avila et al. |
| 11,130,816 B2 | 9/2021 | Pan et al. |
| 11,142,575 B2 | 10/2021 | Blank et al. |
| 11,160,874 B2 | 11/2021 | Avila et al. |
| 11,186,638 B2 | 11/2021 | Snell et al. |
| 12,110,338 B2 | 10/2024 | Pan et al. |
| 2002/0102208 A1 | 8/2002 | Chinn et al. |
| 2002/0187526 A1 | 12/2002 | Ruben et al. |
| 2002/0193572 A1 | 12/2002 | Leung et al. |
| 2003/0082749 A1 | 5/2003 | Sun et al. |
| 2004/0002587 A1 | 1/2004 | Watkins et al. |
| 2004/0132101 A1 | 7/2004 | Lazar et al. |
| 2005/0058641 A1 | 3/2005 | Siemionow |
| 2005/0107575 A1 | 5/2005 | Devisser et al. |
| 2005/0107595 A1 | 5/2005 | Cairns et al. |
| 2005/0238649 A1 | 10/2005 | Doronina et al. |
| 2007/0092940 A1 | 4/2007 | Eigenbrot et al. |
| 2007/0248600 A1 | 10/2007 | Hansen et al. |
| 2008/0038260 A1 | 2/2008 | Ponath et al. |
| 2008/0311134 A1 | 12/2008 | Junutula et al. |
| 2010/0190247 A1 | 7/2010 | Lazar et al. |
| 2010/0226923 A1 | 9/2010 | Rao et al. |
| 2010/0260751 A1 | 10/2010 | Raju et al. |
| 2010/0286067 A1 | 11/2010 | Defrees |
| 2011/0191867 A1 | 8/2011 | Natunen et al. |
| 2011/0263828 A1 | 10/2011 | Wong et al. |
| 2012/0251541 A1 | 10/2012 | Baurin et al. |
| 2014/0271676 A1 | 9/2014 | Pan et al. |
| 2014/0294867 A1 | 10/2014 | Pan et al. |
| 2015/0079070 A1 | 3/2015 | Pan et al. |
| 2015/0099861 A1 | 4/2015 | Snell et al. |
| 2016/0060354 A1 | 3/2016 | Avila et al. |
| 2016/0136299 A1 | 5/2016 | Avila et al. |
| 2016/0244523 A1 | 8/2016 | Blank et al. |
| 2017/0107276 A9 | 4/2017 | Pan et al. |
| 2017/0173175 A1 | 6/2017 | Boons |
| 2017/0267774 A1 | 9/2017 | Pan et al. |
| 2017/0369584 A1 | 12/2017 | Pan et al. |
| 2018/0100010 A1 | 4/2018 | Pan et al. |
| 2018/0237522 A1 | 8/2018 | Snell et al. |
| 2019/0060481 A1 | 2/2019 | Avila et al. |
| 2019/0233531 A1 | 8/2019 | Pan et al. |
| 2020/0140564 A1 | 5/2020 | Pan et al. |
| 2021/0147524 A1 | 5/2021 | Pan et al. |
| 2022/0098299 A1 | 3/2022 | Blank et al. |
| 2022/0153840 A1 | 5/2022 | Qiu et al. |
| 2022/0153841 A1 | 5/2022 | Snell et al. |

FOREIGN PATENT DOCUMENTS

| | | | |
|---|---|---|---|
| CN | 101065151 A | | 10/2007 |
| CN | 102812039 A | | 12/2012 |
| CN | 103626884 A | | 3/2014 |
| CN | 104684930 A | | 6/2015 |
| CN | 106795220 A | | 5/2017 |
| EP | 0120694 A2 | | 10/1984 |
| EP | 0125023 A1 | | 11/1984 |
| EP | 0239400 A2 | | 9/1987 |
| EP | 0396387 A2 | | 11/1990 |
| EP | 0403156 A1 | | 12/1990 |
| EP | 0519596 A1 | | 12/1992 |
| EP | 0706799 A2 | | 4/1996 |
| EP | 0194276 B2 | | 1/2002 |
| EP | 2233499 A1 | | 9/2010 |
| EP | 2755999 A2 | | 7/2014 |
| EP | 2895513 A1 | | 7/2015 |
| EP | 2970469 A1 | | 1/2016 |
| EP | 2983701 A2 | | 2/2016 |
| EP | 3063174 A2 | | 9/2016 |
| EP | 3129067 A1 | | 2/2017 |
| EP | 3204425 A2 | | 8/2017 |
| EP | 3366705 A1 | | 8/2018 |
| EP | 3424956 A1 | | 1/2019 |
| EP | 3799887 A1 | | 4/2021 |
| JP | H03-219896 A | | 9/1991 |
| JP | 2001-521909 A | | 11/2001 |
| JP | 2005-538706 A | | 12/2005 |
| JP | 2006-197930 A | | 8/2006 |
| JP | 2007-525443 A | | 9/2007 |
| JP | 2007-536902 A | | 12/2007 |
| JP | 2008-533993 A | | 8/2008 |
| JP | 2008-537941 A | | 10/2008 |
| JP | 2008-543317 A | | 12/2008 |
| JP | 2009-540828 A | | 11/2009 |
| JP | 2010-510801 A | | 4/2010 |
| JP | 2010-512306 A | | 4/2010 |
| JP | 2010-514460 A | | 5/2010 |
| JP | 2011-517954 A | | 6/2011 |
| JP | 2012-522008 A | | 9/2012 |
| JP | 2012-254996 A | | 12/2012 |
| JP | 2014-527802 A | | 10/2014 |
| JP | 65-99911 B2 | | 10/2019 |
| RU | 2006138181 A | | 6/2008 |
| RU | 2392324 C2 | | 6/2010 |
| UA | 40611 U | | 4/2009 |
| WO | WO 1986/001533 A1 | | 3/1986 |
| WO | WO 1988/007089 A1 | | 9/1988 |
| WO | WO 1989/012624 A2 | | 12/1989 |
| WO | WO 1991/014438 A1 | | 10/1991 |
| WO | WO 1992/003918 A1 | | 3/1992 |
| WO | WO 1992/008495 A1 | | 5/1992 |
| WO | WO 1993/011161 A1 | | 6/1993 |
| WO | WO 1994/009817 A1 | | 5/1994 |
| WO | WO 1994/026087 A2 | | 11/1994 |
| WO | WO 1996/014339 A1 | | 5/1996 |
| WO | WO 1997/037016 A1 | | 10/1997 |
| WO | WO 1998/005787 A1 | | 2/1998 |
| WO | WO 1998/023289 A1 | | 6/1998 |
| WO | WO 1998/052976 A1 | | 11/1998 |
| WO | WO 1999/022764 A1 | | 5/1999 |
| WO | WO 1999/051642 A1 | | 10/1999 |
| WO | WO 1999/058572 A1 | | 11/1999 |
| WO | WO 2000/009560 A2 | | 2/2000 |
| WO | WO 2000/032767 A1 | | 6/2000 |
| WO | WO 2000/034317 A2 | | 6/2000 |
| WO | WO 2000/042072 A2 | | 7/2000 |
| WO | WO 2002/002781 A1 | | 1/2002 |
| WO | WO 2002/044215 A2 | | 6/2002 |
| WO | WO 2002/060919 A2 | | 8/2002 |
| WO | WO 2003/074569 A2 | | 9/2003 |
| WO | WO 2004/006955 A1 | | 1/2004 |
| WO | WO 2004/009823 A1 | | 1/2004 |
| WO | WO 2004/016750 A2 | | 2/2004 |
| WO | WO 2004/029207 A2 | | 4/2004 |
| WO | WO 2004/035752 A2 | | 4/2004 |
| WO | WO 2004/063351 A2 | | 7/2004 |
| WO | WO 2004/074455 A2 | | 9/2004 |
| WO | WO 2004/099249 A2 | | 11/2004 |
| WO | WO 2005/000892 A2 | | 1/2005 |
| WO | WO 2005/017148 A1 | | 2/2005 |
| WO | WO 2005/018572 A2 | | 3/2005 |
| WO | WO 2005/040217 A2 | | 5/2005 |
| WO | WO 2005/047327 A2 | | 5/2005 |
| WO | WO 2005/070963 A1 | | 8/2005 |
| WO | WO 2005/077981 A2 | | 8/2005 |
| WO | WO 2005/092925 A2 | | 10/2005 |
| WO | WO 2005/111225 A1 | | 11/2005 |
| WO | WO 2005/123780 A2 | | 12/2005 |
| WO | WO 2006/019447 A1 | | 2/2006 |

(56) References Cited

FOREIGN PATENT DOCUMENTS

| | | |
|---|---|---|
| WO | WO 2006/036922 A2 | 4/2006 |
| WO | WO 2006/047350 A2 | 5/2006 |
| WO | WO 2006/085967 A2 | 8/2006 |
| WO | WO 2006/105021 A2 | 10/2006 |
| WO | WO 2006/105338 A2 | 10/2006 |
| WO | WO 2006/138739 A2 | 12/2006 |
| WO | WO 2007/005786 A2 | 1/2007 |
| WO | WO 2007/115813 A1 | 10/2007 |
| WO | WO 2008/065543 A2 | 6/2008 |
| WO | WO 2008/086006 A2 | 7/2008 |
| WO | WO 2008/091954 A2 | 7/2008 |
| WO | WO 2008/094176 A2 | 8/2008 |
| WO | WO 2009/052249 A1 | 4/2009 |
| WO | WO 2009/099728 A1 | 8/2009 |
| WO | WO 2009/130198 A2 | 10/2009 |
| WO | WO 2010/027797 A1 | 3/2010 |
| WO | WO 2010/111633 A2 | 9/2010 |
| WO | WO 2011/109400 A2 | 9/2011 |
| WO | WO 2012/012737 A2 | 1/2012 |
| WO | WO 2012/020065 A1 | 2/2012 |
| WO | WO 2012/113863 A1 | 8/2012 |
| WO | WO 2012/125402 A2 | 9/2012 |
| WO | WO 2013/037484 A2 | 3/2013 |
| WO | WO 2014/043361 A1 | 3/2014 |
| WO | WO 2014/164503 A1 | 10/2014 |
| WO | WO 2014/164534 A2 | 10/2014 |
| WO | WO 2015/066379 A2 | 5/2015 |
| WO | WO 2015/143091 A1 | 9/2015 |
| WO | WO 2015/157446 A1 | 10/2015 |
| WO | WO 2016/057769 A2 | 4/2016 |
| WO | WO 2016/057769 A3 | 6/2016 |

OTHER PUBLICATIONS

Sydow et al., "Structure-Based Prediction of Asparagine and Aspartate Degradation Sites in Antibody Variable Regions", PLoS One, Jun. 24, 2014, vol. 9, No. 6, p. e100736.

Wang et al., "Potential aggregation prone regions in biotherapeutics: A survey of commercial monoclonal antibodies", MABS, May 2009, vol. 1, No. 3, pp. 254-267.

"The Research on the Functional Expression and Many-Sided Control of the *Homo sapiens* Antibody", pp. 1171-1180. (1998).

"Nippon Nogeikagaku Kaishi", pp. 9-18. (1998).

Al-Lazikani et al., "Standard Conformations for the Canonical Structures of Immunoglobulins", Journal of Molecular Biology, vol. 273, No. 4, pp. 927-948. (Nov. 7, 1997).

Anthony et al., "Identification of a Receptor Required for the Anti-Inflammatory Activity of IVIG", Proceedings of the National Academy of Sciences, vol. 105, No. 50, pp. 19571-19578. (Dec. 16, 2008).

Anthony et al., "Recapitulation of IVIG Anti-Inflammatory Activity with a Recombinant IgG Fc", Science, vol. 320, No. 5874, pp. 373-376. (Apr. 18, 2018).

Anwer et al., "Synthetic Glycopeptide-Based Delivery Systems for Systemic Gene Targeting to Hepatocytes", Pharmaceutical Research, vol. 17, No. 4, pp. 451-459. (Apr. 1, 2000).

Armour, et al. "Recombinant Human IgG Molecules Lacking Fc gamma Receptor I Binding And Monocyte Triggering Activities", European Journal of Immunology, vol. 29, No. 8, pp. 2613-2624, Aug. 1, 1999.

Ashkenazi, et al., "Pancreatic Islet Xenograft Survival in Mice is Extended by a Combination of Alpha-1-Antitrypsin and Single-Dose Anti-CD4/CD8 Therapy", PloS one, vol. 8, Issue 5, e63625, 10 Pages, 2013.

Axup et al., "Synthesis of Site-Specific Antibody-Drug Conjugates Using Unnatural Amino Acids", Proceedings of the National Academy of Sciences, vol. 109, No. 40, pp. 16101-16106. (Oct. 2, 2012).

Bause et al., "Primary Structural Requirements for N-Glycosylation of Peptides in Rat Liver", FEBS Letters, vol. 108, No. 2, pp. 341-344. (Dec. 1979).

Boeggeman et al., "Direct Identification of Nonreducing GlcNAc Residues on N-Glycans of Glcoproteins Using a Novel Chemoenzymatic Method", Bioconjugate Chemistry, vol. 18, No. 3, pp. 806-814. (Mar. 20, 2007).

Boeggeman et al., "Site Specific Conjugation of Fluoroprobes to the Remodeled Fc N-Glycans of Monoclonal Antibodies Using Mutant Glycosyltransferases: Application for Cell Surface Antigen Detection", Bioconjugate Chemistry, vol. 20, No. 6, pp. 1228-1236. (Jun. 17, 2009).

Brinkmann et al., "Phage Display Of Disulfide-Stabilized Fv Fragments", Journal of Immunological Methods, vol. 182, No. 1, pp. 41-50. (May 11, 1995).

Carey et al., "Advanced Organic Chemistry", Plenum Press, New York and London, (p. 21) 3 Pages. (1978).

Carrasquillo et al., "Improved Imaging of Metastatic Melanoma with High Dose 9.2. 27 In-111 Monoclonal Antibody", Abstract No. 276, Journal of Nuclear Medicine, vol. 26, No. 5, pp. 67. (1985).

Carter et al., "Antibody-Drug Conjugates for Cancer Therapy", The Cancer Journal, vol. 14, No. 3, pp. 154-169. (May 1, 2008).

Cervigni et al., "Synthesis of Glycopeptides and Lipopeptides by Chemoselective Ligation", Angewandte Chemie International Edition in English, vol. 35, No. 11, pp. 1230-1232. (Jun. 17, 1996).

Chan et al., "Therapeutic Antibodies for Autoimmunity and Inflammation", Nature Reviews Immunology, vol. 10, No. 5, pp. 301-316. (May 1, 2010).

Chari Ravi V.J., "Targeted Cancer Therapy: Conferring Specificity to Cytotoxic Drugs", Accounts of Chemical Research, vol. 41, No. 1, pp. 98-107. (Jan. 1, 2008).

Chen et al., "In Vivo Targeting of B-Cell Lymphoma with Glycan Ligands of CD22", Blood, vol. 115, No. 23, pp. 4778-4786. (Jun. 10, 2010).

Chen et al., "Targeting B Lymphoma with Nanoparticles Bearing Glycan Ligands of CD22", Leukemia & Lymphoma, vol. 53, No. 2, pp. 208-210. (Feb. 1, 2012).

Chen, et al.m "Tolerance in the Mouse to Major Histocompatibility Complex-Mismatched Heart Allografts, and to Rat Heart Xenografts, using Monoclonal Antibodies to CD4 and CD8*", European Journal of Immunology, vol. 22, No. 3, pp. 805-810, 1992.

Cobos-Correa et al., "Membrane-Bound FRET Probe Visualizes MMP12 Activity in Pulmonary Inflammation", Nature Chemical Biology, vol. 5, No. 9, pp. 628-663. (Sep. 2009).

Doronina et al., "Development of Potent Monoclonal Antibody Auristatin Conjugates for Cancer Therapy", Nature Biotechnology, vol. 21, No. 7, pp. 778-784. (Jul. 2003).

Ducry et al., "Antibody-Drug Conjugates: Linking Cytotoxic Payloads to Monoclonal Antibodies", Bioconjugate Chemistry, vol. 21, No. 1, pp. 5-13. (Sep. 21, 2010).

Eaton, "Construction And Characterization of An Active Factor VIII Variant Lacking the Central One-Third of the Molecule", Biochemistry, Dec. 30, 1986, 25(26): 8343-8347.

Ebersbach et al., "Affilin-Novel Binding Molecules Based on Human Gamma-B-crystallin, An All Beta-Sheet Protein", Journal On Molecular Biology, vol. 372, No. 1, pp. 172-185. (2007).

Extended European Search Report received for European Patent Application No. 18166377.4, mailed on May 16, 2018, 7 Pages.

Extended European Search Report received for European Patent Application No. 18187892.7, mailed on Nov. 19, 2018, 9 Pages.

Feige et al., "Structure of the Murine Unglycosylated IgG1 Fc Fragment", Journal of Molecular Biology, vol. 391, Issue 3, pp. 599-608. (Aug. 21, 2009).

Fuss, et al., "Nonclassical CD1d-Restricted NK T Cells that Produce IL-13 Characterize an Atypical Th2 Response in Ulcerative Colitis", The Journal of clinical Investigation, vol. 113, No. 10, pp. 1490-1497, 2004.

Ganesan et al., "Rapid and Efficient Clearance of Blood-borne Virus by Liver Sinusoidal Endothelium", PLoS Pathogens, vol. 7, No. 9, e1002281, pp. 1-11. (Sep. 29, 2011).

Gehrig et al., "Spatially Resolved Monitoring of Neutrophil Elastase Activity with Ratiometric Fluorescent Reporters", Angewandte Chemie International Edition, vol. 51, No. 25, pp. 6258-6261. (May 3, 2012).

Getts, et al., "Current landscape for T-cell Targeting in Autoimmunity and Transplantation", Immunotherapy, vol. 3, No. 7, pp. 853-870, 2011.

(56) References Cited

OTHER PUBLICATIONS

Gion et al., "Expression of antibodies using single open reading frame (sORF) vector design: Demonstration of manufacturing feasibility.", mAbs, vol. 5, No. 4, XP055258379, pp. 595-607. (May 31, 2013).

Giudicelli et al., "IMGT/V-QUEST: IMGT Standardized Analysis of the Immunoglobulin (IG) and T Cell Receptor (TR) Nucleotide Sequences", Cold Spring Harbor Protocols, vol. 6, pp. 58-78. (Jun. 1, 2011).

Grabulovski et al., "A Novel Non-immunogenic Fyn SH3-derived Binding Protein with Tumor Vascular Targeting Properties", Journal of Biological Chemistry, vol. 282, No. 5, pp. 3196-3204. (2007).

Guan et al., "Homogeneous Immunoconjugates for Boron Neutron-capture Therapy: Design, Synthesis, and Preliminary Characterization", Proceedings of the National Academy of Sciences vol. 95, No. 22, pp. 13206-13210. (Oct. 2, 1998).

Hanashima et al., "Synthesis of a Sialic Acid r(2-3) Galactose Building Block and Its Use in a Linear Synthesis of Sialyl Lewis X", Organic Letters, vol. 9, No. 9, pp. 1777-1779. (Apr. 6, 2007).

Hatakeyama et al., "Targeted Drug Delivery To Tumor Vasculature By A Carbohydrate Mimetic Peptide", Proceedings of the National Academy of Sciences, vol. 108, No. 49, pp. 19587-19592. (Dec. 6, 2011).

He et al., "Chemoenzymatic Synthesis of New Fluorescent Sialyl Conjugates", Poster, Biotrans Institut fur Organische Chemie und Biochemie, Technische Universitat Darmstadt, 1 Page. (Jan. 1, 2009).

Heidecke et al., "Alpha-beta T Cell Receptor-directed Therapy in Rat Allograft Recipients", Transplantation, vol. 61, No. 6, pp. 948-956. (1996).

Heidecke et al., "Induction Of Long-Term Rat Renal Allograft Survival By Pretransplant T Cell Receptor-α/β-Targeted Therapy", Transplantation, vol. 61, No. 2, pp. 336-339. (1996).

Hodoniczky et al., "Control of Recombinant Monoclonal Antibody Effector Functions by Fc N-glycan Remodeling in Vitro", Biotechnology Progress, vol. 21, No. 6, pp. 1644-1652. (Nov.-Dec. 2005).

Hong et al., "β-Glucan Functions as an Adjuvant for Monoclonal Antibody Immunotherapy by Recruiting Tumoricidal Granulocytes as Killer Cells", Cancer Research, vol. 63, No. 24, pp. 9023-9031. (Dec. 15, 2003).

Hosoguchi et al., "An Efficient Approach to the Discovery of Potent Inhibitors Against Glycosyltransferases", Journal of Medicinal Chemistry vol. 53, No. 15, pp. 5607-5619. (Jul. 2010).

Hudak et al., "Protein Glycoengineering Enabled by the Versatile Synthesis of Aminooxy Glycans and the Genetically Encoded Aldehyde Tag", Journal of the American Chemical Society, vol. 133, No. 40, pp. 16127-16135. (Aug. 25, 2011).

International Search Report and Written Opinion received for PCT Patent Application No. PCT/EP2012/003819, mailed on Jul. 17, 2013, 20 Pages.

International Search Report and Written Opinion received for PCT Patent Application No. PCT/US2014/022623, mailed on Jul. 31, 2014, 11 Pages.

International Search Report and Written Opinion received for PCT Patent Application No. PCT/US2014/022728, mailed on Oct. 9, 2014, 11 Pages.

International Search Report and Written Opinion received for PCT Patent Application No. PCT/US2013/059481, mailed on Feb. 7, 2014, 11 Pages.

International Search Report and Written Opinion received for PCT Patent Application No. PCT/US2015/021342, mailed on Jun. 8, 2015, 11 Pages.

International Search Report and Written Opinion received for PCT Patent Application No. PCT/US2015/054651, mailed on Apr. 20, 2016, 16 Pages.

Jassal et al., "Sialylation of Human IgG-Fc Carbohydrate by Transfected Rat α2,6-Sialyltransferas", Biochemical and Biophysical Research Communications, vol. 286, Issue 2, pp. 243-249. (Aug. 17, 2001).

Jefferis Roy, "Isotype and Glycoform Selection for Antibody Therapeutics", Archives of Biochemistry and Biophysics, vol. 526, Issue 2, pp. 159-166. (Oct. 15, 2012).

Jones et al., "Proteinase mutants of *Saccharomyces cerevisiae*", Genetics, vol. 85, No. 1, pp. 23-33. (Jan. 1977).

Jung et al., "Prevention And Therapy Of Experimental Autoimmune Neuritis By An Antibody Against T Cell Receptors-Alpha/Beta", The Journal of Immunology, vol. 148, No. 12, pp. 3768-3775. (1992).

Junutula et al., "Engineered Thio-Trastuzumab-DM1 Conjugate with an Improved Therapeutic Index to Target Human Epidermal Growth Factor Receptor 2—Positive Breast Cancer", Clinical Cancer Research: an Official Journal of the American Association for Cancer Research, abstract, pp. 4769-4778. (Oct. 1, 2010).

Junutula et al., "Rapid Identification of Reactive Cysteine Residues for Site-Specific Labeling of Antibody-Fabs", Journal of Immunological Methods, vol. 332, Issues 1-2, pp. 41-52. (Mar. 20, 2008).

Junutula et al., "Site-Specific Conjugation of a Cytotoxic Drug to an Antibody Improves the Therapeutic Index", Nature Biotechnology, vol. 26, No. 8, pp. 925-932. (Aug. 1, 2008).

Kaneko et al., "Anti-Inflammatory Activity of Immunoglobulin G Resulting from Fc Sialylation", Science, vol. 313, No. 5787, pp. 670-673. (Aug. 4, 2006).

Kawasaki et al., "Targeted Delivery of Lipid Antigen to Macrophages via the CD169/sialoadhesin Endocytic Pathway Induces Robust Invariant Natural Killer T Cell Activation", Proceedings of the National Academy of Sciences, vol. 110, No. 19, pp. 7826-7831. (May 7, 2013).

Khidekel et al., "A Chemoenzymatic Approach toward the Rapid and Sensitive Detection of 0-GicNAc Posttranslational Modifications", Journal of the American Chemical Society, vol. 125, No. 52, pp. 16162-16163. (Dec. 31, 2015).

Kingsman et al., "Replication In Saccharomyces Cerevisiae Of Plasmid pBR313 Carrying DNA From The Yeast trpl Region", Gene, vol. 7, No. 2, pp. 141-152. (1979).

Knight, et al., "Clinical Evaluation Of Induction Immunosuppression With A Murine Igg2b Monoclonal Antibody (BMA 031) Directed Toward The Human Alpha/Beta-T Cell Receptor", Transplantation, vol. 57, No. 11, pp. 1581-1588, 1994.

Koide et al., "Monobodies: Antibody Mimics Based on the Scaffold of the Fibronectin Type III Domain", Methods in Molecular Biology, vol. 352, pp. 95-109. (2007).

Koulmanda, et al., "Prolonged Survival of Fetal Pig Islet Xenografts in Mice Lacking the Capacity for an Indirect Response", Xenotransplantation, vol. 11, No. 6, pp. 525-530, Nov. 11, 2004.

Krapp et al., "Structural Analysis of Human IgG-Fc Glycoforms Reveals a Correlation Between Glycosylation and Structural Integrity", Journal of Molecular Biology, vol. 325, Issue 5, pp. 979-989. (Jan. 31, 2003).

Krehenbrink et al., "Artificial Binding Proteins (Affitins) as Probes for Conformational Changes in Secretin PulD", Journal of Molecular Biology, vol. 383, No. 5, pp. 1058-1068. (2008).

Labrijn et al., "When Binding is Enough: Nonactivating Antibody Formats", Current Opinion in Immunology, vol. 20, Issue 4, pp. 479-485. (Aug. 2008).

Laguzza et al., "New Antitumor Monoclonal Antibody-Vinca Conjugates LY203725 and Related Compounds: Design, Preparation, and Representative In Vivo Activity", Journal of Medicinal Chemistry, vol. 32, No. 3, pp. 548-555. (Mar. 1989).

Lavasani, et al., "Monoclonal Antibody against T-Cell Receptor αβ Induces Self- Tolerance in Chronic Experimental Autoimmune Encephalomyelitis", Scandinavian Journal of Immunology, vol. 65, No. 1, pp. 39-47, 2007.

Lepenies et al., "Targeting C-Type Lectin Receptors with Multivalent Carbohydrate Ligands", Advanced Drug Delivery Reviews, vol. 65, No. 9, pp. 1271-1281. (Aug. 1, 2013).

Leung et al., "The Effects of Domain Deletion, Glycosylation, and Long IgG 3 Hinge on the Biodistribution and Serum Stability Properties of a Humanized IgG Immunoglobulin, hLL2, and Its Fragments", Clinical Cancer Research, vol. 5, No. 10, pp. 3106s-3117s. (Oct. 1999).

Li et al., "The Preparation of Well-Defined Antibody—Drug Conjugates Through Glycan Remodeling and Strain Promoted Azide-

(56) References Cited

OTHER PUBLICATIONS

Alkyne Cycloadditions", Angewandte Chemie International Edition, vol. 53, No. 2, pp. 7179-7182. (May 23, 2014).
Lund et al., "Multiple Interactions Of IgG With Its Core Oligosaccharide Can Modulate Recognition By Complement And Human Fc γ Receptor I And Influence The Synthesis Of Its Oligosaccharide Chains", The Journal of Immunology, vol. 157, Issue 11, pp. 4963-4969. (Dec. 1, 1996).
Maeda, et al., "Exacerbation of Established Collagen-Induced Arthritis in Mice Treated with an Anti-T Cell Receptor Antibody", Arthritis & Rheumatism, vol. 37, No. 3, pp. 406-413, Mar. 1994.
Martin Andrew C.R., "Protein Sequence and Structure Analysis of Antibody Variable Domains", Chapter 3 of Antibody Engineering, vol. 2, Kontermann and Dubel Eds., Springer-Verlag, pp. 33-51. (2010).
Mattner et al., "Exogenous and Endogenous Glycolipid Antigens Activate NKT Cells During Microbial Infections", Nature 434, No. 7032, pp. 525-529. (Mar. 2005).
McCarthy et al., "Chemoenzymatic Synthesis of Immunogenic Meningococcal Group C Polysialic Acid-Tetanus Hc Fragment Glycoconjugates", Glycoconjugate Journal, vol. 30, Issue 9, pp. 857-870. (Dec. 2013).
Medina et al., "N-Acetylgalactosamine-Functionalized Dendrimers as Hepatic Cancer Cell-Targeted Carriers", Biomaterials, vol. 32, No. 17, pp. 4118-4129. (Jun. 1, 2011).
Monnier et al., "Glucosepane: A Poorly Understood Advanced Glycation End Product of Growing Importance for Diabetes and its Complications", Clinical Chemistry and Laboratory Medicine, vol. 52, No. 1, pp. 21-32. (Jan. 1, 2014).
Murray et al., "Imaging Findings and Pharmacokinetics of 111-Indium ZME-018 Monoclonal Antibody (MoAb) in Malignant Melanoma", Abstract No. 55, Journal of Nuclear Medicine, vol. 26, No. 5, P16, p. 16. (May 1, 1985).
Ngalle et al., "Strain-Promoted Alkyne-Azide Cycloadditions (SPAAC) Reveal New Features of Glycoconjugate Biosynthesis", ChemBioChem, vol. 12, No. 12, XP055182162, pp. 1912-1921. (Aug. 16, 2011).
Nixon et al., "Engineered Protein Inhibitors of Proteases", Current Opinion in Drug Discovery and Development, vol. 9, No. 2, pp. 261-268. (2006).
North et al., "A New Clustering Of Antibody Cdr Loop Conformations", Journal of Molecular Biology, vol. 406, No. 2, pp. 228-256. (2011).
Nygren et al., "Alternative Binding Proteins: Affibody Binding Proteins Developed From a Small Three-Helix Bundle Scaffold", vol. 275, No. 11, pp. 2668-2676. (2008).
Page et al., "Biologics in Organ Transplantation", Transplant International, vol. 25, No. 7, pp. 707-719. (2012).
Piatesi et al., "Immunological Optimization of a Generic Hydrophobic Pocket for High Affinity Hapten Binding and Diels—Alder Activity", ChemBioChem, vol. 5, Issue 4, pp. 460-466. (Apr. 2, 2004).
Polakis, "Arming Antibodies for Cancer Therapy", Current Opinion in Pharmacology, vol. 5, Issue 4, pp. 382-387. (Aug. 2005).
Qu et al., "Carbohydrates Engineered at Antibody Constant Domains can be used for Site-Specific Conjugation of Drugs and Chelates", Journal of Immunological Methods, vol. 213, Issue 2, pp. 131-144. (Jun. 1998).
Radaev et al., "The Structure of a Human Type III Fcg Receptor in Complex with Fc", Journal of Biological Chemistry, vol. 276, No. 19, pp. 16469-16477. (May 11, 2001).
Raju et al., "Glycoengineering of Therapeutic Glycoproteins: In Vitro Galactosylation and Sialylation of Glycoproteins with Terminal Nacetylglucosamine and Galactose Residues", Biochemistry, vol. 40, No. 30, (Abstract), pp. 8868-8876. (Jul. 31, 2001).
Renaudet et al., "On-Bead Synthesis and Binding Assay of Chemoselectively Template-Assembled Multivalent Neoglycopeptides", Organic and Biomolecular Chemistry, vol. 4, No. 13, pp. 2628-2636. (2006).
Ridgway, Anthony A.G., Introduction of Vector into Host Cells, Mammalian Expression Vectors, Chapter 24.2, pp. 470-472, 1988.

Roche Diagnostics, "Alpha-2,6, Sialyltransferase Cat. No. 07 012 250 103 (Data sheet)", XP002727803, Retrieved From URL: https://cssportal.roche.com/LFR_PublicDocs/ras/07012250103_en_02.pdf, (May 2013).
Roitt, Immunology, 5th edition, Chapter 6, pp. 110-111 (2000), with English translation.
Roux et al., "Comparisons of the Ability of Human IgG3 Hinge Mutants, IgM, IgE, and IgA2, to Form Small Immune Complexes: A Role for Flexibility and Geometry", Journal of Immunology, vol. 161, No. 8, pp. 4083-4090. (Oct. 15, 1998).
Rudikoff et al., "Single Amino Acid Substitution Altering Antigen-Binding Specificity", Proceedings of the National Academy of Sciences of the United States of America, vol. 79, pp. 1979-1983. (Mar. 1, 1982).
Sakarellos-Kaitsiotis et al., "Design, Synthesis and Binding Assays of Sialic Acid and Sialyl-Saccharide Conjugates to Lectins and Influenza H1 N1 Virus-Design, Synthesis and Binding Assays of Sialic Acid and Sialyl-Saccharide Conjugates to Lectins and Influenza H1N1 Virus", Abstract No. 069, Journal of Peptide Science, vol. 18, Supplement 1, p. S52. (2012).
Sazinsky et al., "Aglycosylated Immunoglobulin G1 Variants Productively Engage Activating Fc Receptors", Proceedings of the National Academy of Sciences of the United States of America, vol. 105, No. 51, pp. 20167-20172. (Dec. 23, 2008).
Scharpf et al., "Immunomodulation With Anti-αβ T-Cell Receptor Monoclonal Antibodies In Combination With Cyclosporine A Improves Regeneration In Nerve Allografts", Microsurgery: Official Journal of the International Microsurgical Society and the European Federation of Societies for Microsurgery, vol. 26, No. 8, pp. 599-607. (2006).
Schorlemmer et al., "Synergistic Effects Of 15-Deoxyspergualin With Cyclosporine And The TCR-Targeted Monoclonal Antibody R73 To Induce Specific Unresponsiveness To Skin Allografts In Rats", Transplantation Proceedings, vol. 27, No. 1, pp. 414-416. (1995).
Schroeder et al., "Structure and Function of Immunoglobulins", The Journal of Allergy and Clinical Immunology, vol. 125, No. 2, Supplement 2, pp. 841-852. (2010).
Sempe, et al., "Anti-α/β T Cell Receptor Monoclonal Antibody Provides an Efficient Therapy for Autoimmune Diabetes in Nonobese Diabetic (NOD) Mice", European Journal of Immunology, vol. 21, No. 5, pp. 1163-1169, 1991.
Shannessy et al., "Labeling of the Oligosaccharide Moieties of Immunoglobulins", Journal of Immunological Methods, vol. 99, Issue 2, pp. 153-161. (May 20, 1987).
Shao et al., "Unprotected Peptides as Building Blocks for the Synthesis of Peptide Dendrimers with Oxime, Hydrazone, and Thiazolidine Linkages.", Journal of the American Chemical Society, vol. 117, No. 14, pp. 3893-3899. (Apr. 1995).
Shearman et al., "Construction, Expression And Characterization Of Humanized Antibodies Directed Against The Human Alpha/Beta T Cell Receptor", The Journal of Immunology, vol. 147, No. 12, pp. 4366-4373. (1991).
Shearman et al., "Construction, Expression, and Biologic Activity of Murine/Human Chimeric Antibodies with Specificity for the Human Alpha/Beta T Cell Receptor", The Journal of Immunology, vol. 146, No. 3, pp. 928-935. (Feb. 1, 1991).
Shields et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604. (Mar. 2, 2001).
Silverman et al., "Multivalent Avimer Proteins Evolved By Exon Shuffling of A Family of Human Receptor Domains", Nature Biotechnology, vol. 23, No. 12, pp. 1556-1561. (Dec. 2005).
Skerra et al., "Alternative Binding Proteins: Anticalins—Harnessing the StructuralPlasticity of the Lipocalin Ligand Pocket to Engineer Novel Binding Activities", The FEBS Journal, vol. 275, No. 11, pp. 2677-2683 (2008).
Stinchcomb et al., "Isolation And Characterisation Of A Yeast Chromosomal Replicator", Nature, vol. 282, No. 5734, pp. 39-43. (Nov. 1, 1979).

(56) References Cited

OTHER PUBLICATIONS

Stumpp et al., "DARPins: A New Generation of Protein Therapeutics", Drug Discovery Today, vol. 13, pp. 15-16. (pp. 695-701.), (2008).
Tachibana, "Study on functional expression of human antibody and its multifaceted control", Journal of the Agricultural Chemical Society of Japan, 72 (10): 1171-1180 (1998).
Teicher B A., "Antibody-Drug Conjugate Targets", Current Cancer Drug Targets, vol. 9, No. 8, pp. 982-1004. (Dec. 9, 2009).
Tschumper et al., "Sequence Of A Yeast DNA Fragment Containing A Chromosomal Replicator And The TRP1 Gene", Gene, vol. 10, No. 2, pp. 157-166. (Jul. 1980).
Wang et al., "Impact of Methionine Oxidation in Human IgG1 Fc on Serum Half-Life of Monoclonal Antibodies", Immunology, vol. 48, No. 6, pp. 860-866. (Mar. 1, 2011).
Wang et al., "Single-Chain Fv With Manifold N-Glycans as Bifunctional Scaffolds for Immunomolecules", Protein Engineering, vol. 11, No. 12, pp. 1277-1283. (Jan. 1, 1998).
Wei et al., "Glycoengineering of Human IgG1-Fc Through Combined Yeast Expression and In Vitro Chemoenzymatic Glycosylation", Biochemistry, vol. 47, No. 39, pp. 10294-10304. (Sep. 2008).
Williams et al., "Humanising Antibodies By CDR Grafting", Antibody Engineering, pp. 319-339. (2010).
Winkler K. et al., "Changing the antigen binding specificity by single point mutations of an anti-p24 (HIV-A21) antibody", Journal of Immunology, vol. 165, No. 8, pp. 4505-4514. (Oct. 15, 2000).
Wright et al., "Genetically Engineered Antibodies: Progress And Prospects", Critical Reviews In Immunology, vol. 12, No. 3-4, pp. 125-168. (1992).
Wu et al., "Humanization of a Murine Monoclonal Antibody by Simultaneous Optimization of Framework and CDR Residues", Journal of Molecular Biology, vol. 294, No. 1, pp. 151-162. (Nov. 19, 1999).
Yamagami et al., "Suppression Of Allograft Rejection With Anti-αβ T Cell Receptor Antibody In Rat Corneal Transplantation1", Transplantation, vol. 67, No. 4, pp. 600-604. (1999).
Yoshino et al., "Depletion Of Alpha/Beta T Cells By A Monoclonal Antibody Against The Alpha/Beta T Cell Receptor Suppresses Established Adjuvant Arthritis, But Not Established Collagen-Induced Arthritis In Rats", Journal of Experimental Medicine, vol. 175, No. 4, pp. 907-915. (1992).
Yu et al., "Interaction between Bevacizumab and Murine VEGF-A: A Reassessment", Investigative Ophthalmology & Visual Science, vol. 49, No. 2, pp. 522-527. (Feb. 2008).
Yu, et al., "Expression and Functional Characterization of FOXP3+ CD4+ Regulatory T Cells in Ulcerative Colitis", Inflammatory Bowel Diseases, vol. 13, No. 2, pp. 191-199, Feb. 1, 2007.
Zevgiti et al., "Sialic Acid and Sialyl-Lactose Glyco-Conjugates: Design, Synthesis andBinding Assays to Lectins and Swine Influenza H1N1 Virus", Journal of Peptide Science, vol. 18, Issue 1, pp. 52-58. (Nov. 3, 2011).
Zhang et al., "Applications of Azide-Based Bioorthogonal Click Chemistry in Glycobiology", Molecules, vol. 18, No. 6, XP055507949, pp. 7145-7159. (Jun. 19, 2013).
Zhou et al., "Bioconjugation by Native Chemical Tagging of C-H Bonds", Journal of theAmerican Chemical Society, vol. 135, No. 35, pp. 12994-12997. (Aug. 22, 2013).
Zhou et al., "Development Of A Simple And Rapid Method For Producing Non-Fucosylated Oligomannose Containing Antibodies With Increased Effector Function", Biotechnology and Bioengineering, vol. 99, No. 3, pp. 652-665. (Feb. 15, 2008).
Zhou et al., "Site-Specific Antibody—Drug Conjugation through Glycoengineering", Bioconjugate Chemistry, vol. 25, No. 3, pp. 510-520. (Mar. 19, 2014).
Zhou et al., "Strategies for Neoglycan Conjugation to Human Acid α-Glucosidase", Bioconjugate Chemistry, vol. 22, No. 4, pp. 741-751. (Apr. 20, 2011).
Zhu et al., "Glycoengineered Acid Alpha-Glucosidase with Improved Efficacy at Correcting the Metabolic Aberrations and Motor Function Deficits in a Mouse Model of Pompe Disease", Molecular Therapy, vol. 17, Issue 6, pp. 954-963. (Jun. 2009).
ATCC, Cercopithecus Aethiops, Accession No. CRL-1650, obtained online Mar. 4, 2021 at: https://www.atcc.org/products/crl-1650.
ATCC, Cercopithecus Aethiops, CVI (ATCC Accession No. CCL-70), 1964, obtained online Mar. 4, 2021 at: https://www.atcc.org/products/ccl-70.
ATCC, Cricetulus Griseus, Accession No. CRL-9096, obtained online Mar. 4, 2021 at: https://www.atcc.org/products/crl-9096.
ATCC, *Homo Sapiens*, Human, Accession No. CRL-1573, obtained online Mar. 4, 2021 at: https://www.atcc.org/products/crl-1573.
Backliwal, et al., Rational Vector Design and Multi-Pathway Modulation of Hek 293e Cells Yield Recombinant Antibody Titers Exceeding 1 G/L By Transient Transfection Under Serum-Free Conditions, Nucleic Acids Research, vol. 36 Issue 15, pp. e96, Sep. 1, 2008.
Boyd, et al., The Effect of the Removal of Sialic Acid, Galactose and Total Carbohydrate on the Functional Activity of Campath-1H, Molecular Immunology, vol. 32, No. 17-18, pp. 1311-1318, Dec. 1, 1995.
Chapman, et al., PEGylated Antibodies and Antibody Fragments for Improved Therapy: A Review, Advanced Drug Delivery Reviews, vol. 54, No. 4, pp. 531-545, 2002.
Cupit, et al., Cloning and Expression of Single Chain Antibody Fragments in *Escherichia coli* and Pichia pastoris, Letters in Applied Microbiology, vol. 29, Issue 5, pp. 273-277, Nov. 1, 1999.
Dailey, et al., Sequences in the Polyomavirus DNA Regulatory Region Involved in Viral DNA Replication and Early Gene Expression, Journal of Virology, vol. 54, No. 3, pp. 739-749, Jun. 1, 1985.
Do, et al., CD4 T Cells Play Important Roles in Maintaining IL-17-Producing γδ T Cell Subsets in Naïve Animals, Immunology and Cell Biology, vol. 90, No. 4, pp. 396-403, Apr. 1, 2012.
Doran, Foreign Protein Production in Plant Tissue Cultures, Current Opinion in Biotechnology, vol. 11, Issue 2, pp. 199-204, Apr. 1, 2000.
Drapeau, et al., Extracellular Insulin Degrading Activity Creates Instability in a CHO-Based Batch-Refeed Continuous Process, Cytotechnology, vol. 15, Issue 1-3, pp. 103-109, Feb. 1, 1994.
Exner, et al., αβTCR+ T Cells Play a Nonredundant Role in The Rejection of Heart Allografts In Mice, Surgery, vol. 126, No. 2, pp. 121-126, 1999.
Gentz, et al., Bioassay for Trans-Activation Using Purified Human Immunodeficiency Virus Tat-Encoded Protein: Trans-Activation Requires Mrna Synthesis, Proceedings of the National Academy of Sciences, vol. 86, No. 3, pp. 821-824, Feb. 1, 1989.
Gonçalves-Sousa, et al., Inhibition of Murine γδ Lymphocyte Expansion and Effector Function by Regulatory αβ T Cells Is Cell-contact-dependent and Sensitive to GITR Modulation, European Journal of Immunology, vol. 40, pp. 61-70, 2010.
Gu, et al., Rapamycin Together With TGF-β1, IL-2 And IL-15 Induces the Generation of Functional Regulatory γδT Cells from Human Peripheral Blood Mononuclear Cells, Journal of Immunological Methods, vol. 402, No. 1-2, pp. 82-87, 2014.
He, et al., γδ T Cell and Other Immune Cells Crosstalk in Cellular Immunity, Journal of Immunology Research, vol. 2014, pp. 1-8, 2014.
Heidecke, et al., Alpha-beta T Cell Receptor-directed Therapy in Rat Allograft Recipients, Transplantation, vol. 61, No. 6, pp. 948-956, Mar. 27, 1996.
Heidecke, et al., Induction of Long-Term Rat Renal Allograft Survival by Pretransplant T Cell Receptor-α/β-Targeted Therapy, Transplantation, vol. 61, No. 2, pp. 336-339, Jan. 27, 1996.
Hoekema, et al., Codon Replacement in the PGK1 Gene of Saccharomyces Cerevisiae: Experimental Approach to Study the Role of Biased Codon Usage in Gene Expression, Molecular and Cellular Biology, vol. 7, No. 8, pp. 2914-2924, Aug. 1, 1987.
International Search Report and Written Opinion received for PCT Patent Application No. PCT/EP2012/003819, mailed on Jul. 7, 2013.
International Search Report and Written Opinion received for PCT Patent Application No. PCT/US2014/063254, mailed on May 4, 2015.

(56) References Cited

OTHER PUBLICATIONS

Keen, et al., Development of a Serum-Free Culture Medium for the Large Scale Production of Recombinant Protein from a Chinese Hamster Ovary Cell Line, Cytotechnology, vol. 17, Issue 3, pp. 153-163, Oct. 1, 1995.

King, et al., Human Peripheral Blood Leucocyte Non-Obese Diabetic-Severe Combined Immunodeficiency Interleukin-2 Receptor Gamma Chain Gene Mouse Model of Xenogeneic Graft-Versus-Host-Like Disease and The Role of Host Major Histocompatibility Complex, Clinical & Experimental Immunology, vol. 157, No. 1, pp. 104-118, 2009.

Kuhns, et al., Deconstructing the Form and Function of The TCR/CD3 Complex, Immunity, vol. 2, No. 2, pp. 133-139, 2006.

Lamb et al., "Rapid Communication: Increased Frequency of TCRγδ+ T Cells in Disease-Free Survivors Following T Cell-Depleted, Partially Mismatched, Related Donor Bone Marrow Transplantation for Leukemia", Journal of Hemptherapy, Mar. 27, 2009, 5(5): 503-509.

Lamb et al., "γδ T Cells: A New Frontier for Immunotherapy?", Biology of Blood and Bone Marrow Transplantation, Mar. 2005, 11(3): 161-168.

Leong, et al., Adapting Pharmacokinetic Properties of a Humanized Anti-Interleukin-8 Antibody for Therapeutic Applications Using Site-Specific Pegylation, Cytokine, vol. 16, Issue 3, pp. 106-119, 2001.

Ma, et al., Characterization of a Recombinant Plant Monoclonal Secretory Antibody and Preventive Immunotherapy in Humans, Nature Medicine, vol. 4, No. 5, pp. 601-606, 1998.

Michishita, et al., Age-Associated Alteration of γδT—Cell Repertoire and Different Profiles of Activation-Induced Death of V δ1 and Vδ2 T Cells, International Journal of Hematology, vol. 94, No. 3, pp. 230-240, 2011.

Mizushima, et al., pEF-BOS, A Powerful Mammalian Expression Vector, Nucleic Acids Research, vol. 18, No. 17, p. 5322, 1990.

Nishimura et al., "Inhibition of skin xenograft rejection by depleting T-cell receptor alpha beta-bearing cells without T-cell receptor gamma delta-bearing cells or natural killer cells by monoclonal antibody", Immunology, Oct. 1994, 83(2): 196-204.

Pear, et al., Production of High-Titer Helper-Free Retroviruses by Transient Transfection, Proceedings of the National Academy of Sciences of the United States of America, vol. 90, No. 18, pp. 8392-8396, 1993.

Pollock, et al., Transgenic Milk as A Method for The Production of Recombinant Antibodies, Journal of Immunological Methods, vol. 231, No. 1-2, pp. 147-157, 1999.

Powrie, Immune Regulation in the Intestine, Annals of the New York Academy of Sciences, vol. 1029, No. 1, pp. 132-141, 2004.

Sánchez, et al., High Cytoplasmic Expression in *E. coli*, Purification, and in vitro Refolding of a Single Chain Fv Antibody Fragment Against the Hepatitis B Surface Antigen, Journal of Biotechnology, vol. 72, Issues 1-2, pp. 13-20, 1999.

Scharfenberg, et al., A Reliable Strategy for The Achievement of Cell Lines Growing in Protein-Free Medium, Animal Cell Technology: Developments Towards the 21st Century, pp. 619-623, 1995.

Snell, et al., Immunosuppression for Lung Transplantation, Drugs, vol. 67, No. 11, pp. 1531-1539, 2007.

Spinozzi, et al., T Lymphocytes Bearing the γδ T Cell Receptor are Susceptible to Steroid-Induced Programmed Cell Death, Scandinavian Journal of Immunology, vol. 41, No. 5, pp. 504-508, 1995.

Stoger, et al., Cereal Crops as Viable Production and Storage Systems for Pharmaceutical scFv Antibodies, Plant Molecular Biology, vol. 42, No. 4, pp. 583-590, 2000.

Svennilson, et al., Novel Approaches in GVHD Therapy, Bone Marrow Transplantation, vol. 35, pp. S65-S67, 2005.

Tao, et al., Studies of Aglycosylated Chimeric Mouse-Human IgG. Role of Carbohydrate in The Structure and Effector Functions Mediated By The Human IgG Constant Region, The Journal of Immunology, vol. 143, No. 8, pp. 2595-2601, 1989.

Ulivieri, et al., T-Cell-Based Immunotherapy of Autoimmune Diseases, Expert Review of Vaccines, vol. 12, No. 3, pp. 297-310, 2013.

Urlaub, et al., Isolation of Chinese Hamster Cell Mutants Deficient in Dihydrofolate Reductase Activity, Proceedings of the National Academy of Sciences of the United States of America, vol. 77, No. 7, pp. 4216-4220, 1980.

Waid, et al., T10B9 Monoclonal Antibody: A Short-Acting Nonstimulating Monoclonal Antibody that Spares γδ T-Cells and Treats and Prevents Cellular Rejection, Drug design, Development and Therapy, vol. 3, pp. 205-212, 2009.

Ward, et al., Binding Activities of a Repertoire of Single Immunoglobulin Variable Domains Secreted from *Escherichia coli*, Nature, vol. 341, No. 6242, pp. 544-546, 1989.

Weir, et al., Formatting Antibody Fragments to Mediate Specific Therapeutic Functions, Biochemical Society Transactions, vol. 30, pp. 512-516, 2002.

Wilson, et al., The Structure of An Antigenic Determinant in A Protein, Cell, vol. 37, No. 3, pp. 767-778, 1984.

\* cited by examiner

FIG. 7

| Mutant | Rationale |
|---|---|
| N93Q | Same uncharged polar amino acid, one carbon longer |
| N93D | Similar in size and H-bonding |
| N93H | Similar H-bonding, slightly bulkier |
| N93S | Uncharged polar amino acid, similar H-bonding, smaller and flexible |
| N93Y | Similar H-bonding, frequently found in CDRs |
| N93A/P94A | Impact of replacing both amino acids |
| N93A | Impact of replacing Asn |
| P94A | Impact of replacing Pro |

ANTI-ALPHA BETA TCR BINDING POLYPEPTIDES WITH REDUCED FRAGMENTATION

RELATED APPLICATIONS

This application is a 35 U.S.C. § 371 filing of International Patent Application No. PCT/US2020/026304, filed Apr. 2, 2020, which claims the benefit of U.S. Provisional Patent Application No. 62/828,601, filed Apr. 3, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 30, 2020, is named 722170_SA9-254US_ST25.TXT and is 32,649 bytes in size.

BACKGROUND

Monoclonal antibodies are an important class of binding polypeptides and biologic therapeutic drugs. In general, polypeptide backbones are highly stable under physiological conditions. Nevertheless, fragmentation of heavy and light chain polypeptides is a major concern with therapeutic monoclonal antibodies.

In general, protein backbones are highly stable under physiological conditions. However, fragmentation may be caused by a variety of mechanisms, e.g., due to the disruption of native covalent bonds, resulting in the cleavage of polypeptide backbones through spontaneous or enzymatic reactions. In addition, specific regions and motifs (e.g., the Asn-Pro motif) may be more susceptible to fragmentation due to amino acid sequence, the flexibility of the two- or three-dimensional polypeptide structure, and incompatible solvent and environmental conditions (e.g., temperature and pH).

Fragmentation may occur at any step during the manufacture or storage of biologic compositions. Because fragmentation may result in reduced potency or the presence of unwanted and potentially immunogenic species, reducing fragmentation is a key consideration in the production of any biologic therapeutic.

Thus, there is a need in the art for antibody compositions with improved stability that demonstrate reduced fragmentation of antibody polypeptide chains during manufacture and subsequent storage.

SUMMARY

The present disclosure provides improved compositions and methods useful for treating T-cell-mediated diseases and disorders. Provided are humanized binding polypeptides that specifically bind the alpha beta T-cell receptor (αβTCR). The anti-αβTCR compositions provided herein are an improvement over known compositions in that the improved compositions comprise at least one amino acid substitution or modification that increases the stability of the binding polypeptide by reducing fragmentation of the light chain variable region. Also provided are methods for treating T-cell-mediated diseases and disorders (e.g., graft-versus-host-disease, autoimmune disease, and graft rejection) with the improved compositions. The methods provided herein generally involve administering to a subject in need thereof an effective amount of a humanized binding polypeptide that specifically binds the αβTCR.

Surprisingly, the instant inventors have found that removal of an Asn clipping site in the light chain of anti-human αβTCR antibody VH31 reduces fragmentation of this antibody. This finding is particularly surprising because the putative Asn clipping site occurs within a complementarity determining region (CDR), and previous attempts at removing Asn clipping sites in an unrelated antibody (i.e., sFLT01) did not prevent antibody fragmentation.

In an aspect, there is provided a binding polypeptide that specifically binds to human αβTCR/CD3 complex, comprising a heavy chain variable region, a light chain variable region, and a constant region, wherein:

the light chain variable region comprises three complementarity determining regions (CDRs) LCDR1, LCDR2, and LCDR3 comprising the amino acid sequences set forth in SEQ ID NOs: 26, 27, and 28, respectively;

SEQ ID NO: 28 comprises the amino acid sequence Q-Q-W-S-S-$X_1$-$X_2$-L-T, wherein $X_1$ is an amino acid selected from the group consisting of Q, D, H, S, Y, and A, and $X_2$ is an amino acid selected from the group consisting of P and A; and the constant region is of human origin.

In certain embodiments, $X_1$ is S.
In certain embodiments, $X_2$ is P.
In certain embodiments, $X_1$ is S, and $X_2$ is P.
In certain embodiments, the light chain variable region further comprises a human light chain framework region set forth in SEQ ID NO: 14.

In certain embodiments, the binding polypeptide has increased stability at pH greater than 5.0 compared to VH31.

In certain embodiments, the binding polypeptide has increased stability at a temperature greater than 4° C. compared to VH31.

In certain embodiments, the heavy chain variable region comprises an amino acid sequence selected from the group consisting of SEQ ID NOs: 7, 12, 13, 15, and 16.

In certain embodiments, the heavy chain variable region comprises an amino acid sequence selected from the group consisting of SEQ ID NO: 7, SEQ ID NO: 12, and SEQ ID NO: 13.

In certain embodiments, the heavy chain variable region comprises an amino acid sequence selected from the group consisting of SEQ ID NO: 15 and SEQ ID NO: 16.

In certain embodiments, the heavy chain variable region comprises the amino acid sequence set forth as SEQ ID NO: 15.

In certain embodiments, the heavy chain variable region comprises the amino acid sequence set forth as SEQ ID NO: 16.

In certain embodiments, the constant region comprises an Fc modification with a modified glycosylation pattern that reduces Fcγ receptor binding.

In certain embodiments, the Fcγ receptor is one or more receptor selected from the group consisting of FcγRIIIa and FcγRI.

In certain embodiments, the Fc modification is selected from the group consisting of N297Q/S298N/Y300S, S298N/T299A/Y300S, and S298N/Y300S.

In certain embodiments, the Fc modification is N297Q/S298N/Y300S.

In certain embodiments, the Fc modification is S298N/T299A/Y300S. In an embodiment, the Fc modification is S298N/Y300S.

In certain embodiments, the binding polypeptide is humanized.

In certain embodiments, the binding polypeptide is a monoclonal antibody.

In certain embodiments, the binding polypeptide is multispecific.

In certain embodiments, the binding polypeptide is bispecific.

In another aspect, there is provided a pharmaceutical composition, comprising a binding polypeptide described herein, and a pharmaceutically acceptable carrier or diluent.

In another aspect, there is provided a formulation comprising a pharmaceutical composition described herein. In certain embodiments, the formulation is a liquid formulation. In certain embodiments, the formulation is a lyophilized formulation.

In another aspect, there is provided a method of treating a subject for a T-cell-mediated disease or disorder, comprising administering to the subject an effective amount of a binding polypeptide or a pharmaceutical composition described herein, such that treatment is achieved. In certain embodiments, the T-cell-mediated disease or disorder is selected from the group consisting of systemic lupus erythematosus (SLE), rheumatoid arthritis (RA), inflammatory bowel disease (IBD), ulcerative colitis (UC), Crohn's disease (CD), multiple sclerosis (MS), scleroderma, type 1 diabetes (T1D), pemphigus vulgaris (PV), psoriasis, atopic dermatitis, celiac disease, chronic obstructive lung disease, Hashimoto's thyroiditis, Graves' disease (thyroid), Sjögren's syndrome, Guillain-Barré syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, Behcet's disease, primary biliary cirrhosis, uveitis, myocarditis, rheumatic fever, ankylosing spondylitis, glomerulonephritis, sarcoidosis, dermatomyositis, myasthenia gravis, polymyositis, alopecia areata, vitilgo, graft-versus host disease (GvHD), and allograft rejection.

In another aspect, there is provided a nucleic acid encoding a binding polypeptide described herein.

In another aspect, there is provided a vector comprising a nucleic acid described herein.

In another aspect, there is provided a cell comprising a nucleic acid described herein. In an embodiment, the cell is a mammalian cell. In an embodiment, the mammalian cell is selected from the group consisting of a Chinese hamster ovary (CHO) cell and a human embryonic kidney (HEK) cell.

BRIEF DESCRIPTION OF THE FIGURES

The foregoing and other features and advantages of the present invention will be more fully understood from the following detailed description of illustrative embodiments taken in conjunction with the accompanying drawings.

FIG. 7 depicts the various VH31 LC amino acid mutations that were made to enhance LC stability.

DETAILED DESCRIPTION

Figure 1:
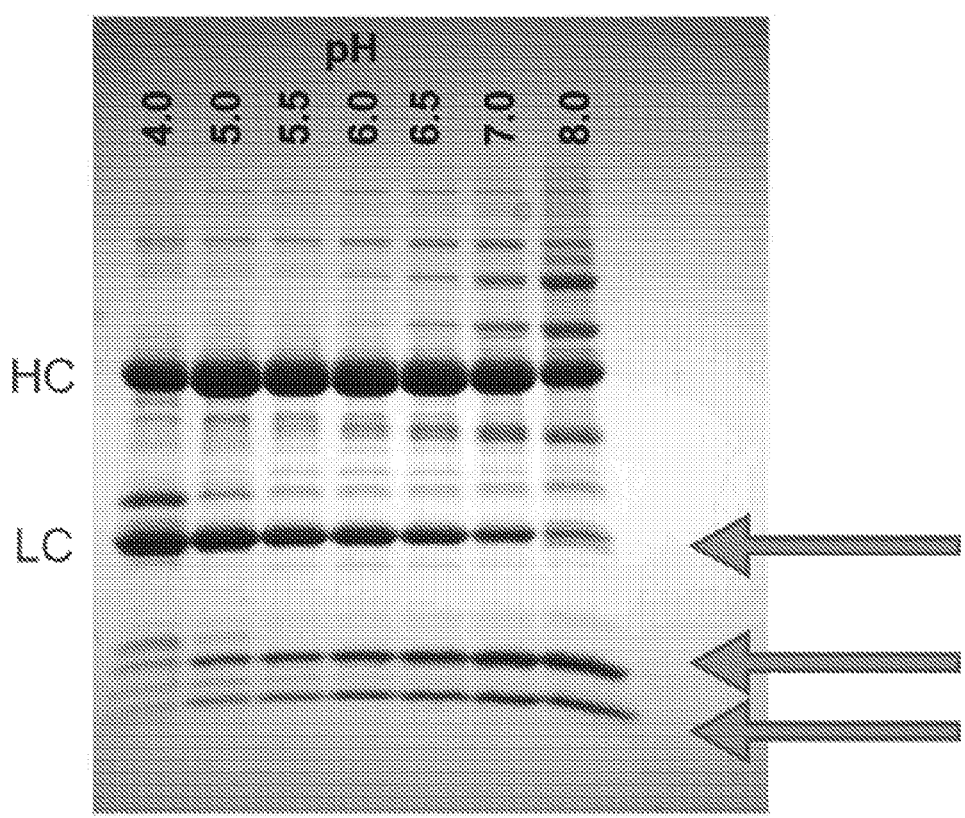
FIG. 1 is a photograph of a protein gel showing the appearance of low molecular weight (LMW) fragments of reference humanized anti-αβTCR antibody VH31 formulated antibody under accelerated conditions involving elevated temperature (45° C.) and the indicated pH for five weeks. HC, heavy chain; LC, light chain.

The present disclosure provides improved compositions and methods for treating T-cell-mediated disorders (e.g., graft-versus-host-disease, autoimmune disease, and allograft rejection). The methods provided herein generally involve administering to a subject in need thereof an effective amount of a humanized binding polypeptide that is specific to the alpha beta T-cell receptor (αβTCR). The anti-αβTCR compositions provided herein are improvement over known compositions in that the improved compositions comprise one or more one amino acid substitution or modification that improves stability of the binding polypeptide by reducing fragmentation of the light chain variable region.

I. Definitions

Unless otherwise stated, all technical and scientific terms used herein have the same meanings as commonly understood by one of ordinary skill in the art to which this disclosure belongs. Any methods and materials similar or equivalent to those described herein can be used in the methods of techniques of the present disclosure. All publications cited herein are incorporated herein by reference in their entirety for the purpose of describing and disclosing the methodologies, reagents, and tools reported in the publications that might be used in connection with the disclosure.

The methods and techniques of the present application are generally performed according to conventional methods well known in the art and as described in various general and more specific references that are cited and discussed throughout the present specification unless otherwise indicated. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M. and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. 1-Ill, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R. and Graham, A., eds. (1997) PCR (Introduction to Biotechniques Series), 2nd ed., Springer-Verlag.

The human αβTCR/CD3 complex is a T-cell receptor complex presented on the surface of T cells. See, Kuhns et al. (2006) Immunity 24:133-139. This complex is targeted by the murine monoclonal antibody BMA031 (see, European patent application EP 0403156; SEQ ID NOs: 1 and 2, incorporated herein by reference in its entirety) and the humanized and stabilized antibodies disclosed herein.

The mouse IgG2b monoclonal antibody BMA031 (Borst et al. (1990) Hum. Immunol. 29(3): 175-88; EP0403156) is specific for the common determinant on the alpha-beta TCR/CD3 complex, and does not bind to the gamma-delta TCR. BMA031 is highly immunosuppressive and is capable of inducing apoptosis of activated T cells via a mechanism of activation-induced cell death (AICD) (Wesselborg et al. (1993) J. Immunol. 150(10): 4338-4345). In vitro it inhibits a mixed lymphocyte reaction and it has shown preliminary clinical efficacy in prevention of graft rejection in a number of solid organ transplant scenarios as well as the treatment of acute graft versus host disease (Kurrle et al. (1989) Transplant Proc. 21(1): 1017-1019). BMA031 does not engage human Fc gamma receptors (FcγR) in the majority of the human population. As such BMA031 does not cause T-cell activation via cross-linking of the T-cell receptor and, therefore, it does not induce T-cell activation or the associated cytokine release. In this regard its profile is highly preferable over that of OKT3. However, BMA031 is a murine antibody and, as such, is not suitable for repeat dosing in human subjects in view of the human anti-mouse antibody (HAMA) response elicited therein.

Several humanized versions of BMA031 have been described (see, for example, WO 2013/037484; EP 0403156; also Shearman et al. (1991) J. Immunol. 147:4366-4373). As noted in EP 0403156, mere CDR grafting was not successful in retaining antigen binding. One clone with significant "civilizing" framework modifications, EUCIV3, successfully bound to T cells; however, as noted in EP 0403156, binding to the αβTCR is not as effective as the parent BMA031 antibody as determined by flow cytometry competition assays. In addition, EUCIV3 was originally generated on a wild-type human IgG1 or IgG4 backbone which still retains FcγR binding. These humanized antibodies therefore allowed for T-cell activation, proliferation and the concomitant cytokine release and as such were significantly different from the original properties of BMA031.

The term "binding protein" or "binding polypeptide," unless indicated otherwise, is used to refer to a polypeptide (e.g., an antibody or antigen-binding fragment thereof) that contains at least one binding site which is responsible for selectively binding to a target antigen of interest (e.g., a human antigen). Exemplary binding sites include an antibody variable domain, a ligand binding site of a receptor, or a receptor binding site of a ligand. In certain aspects, the binding polypeptides described herein comprise multiple (e.g., two, three, four, or more) binding sites.

The term "antibody," unless indicated otherwise, is used to refer to entire antibodies as well as antigen-binding fragments of such antibodies. For example, the term encompasses four-chain IgG molecules, as well as antibody fragments.

As used herein, the term "antibody fragment" refers to portions of an intact full-length antibody, for example, as further described below.

Antibodies may be of any class, such as IgG, IgA, IgE, IgD, or IgM; and of any subclass, such as IgG1 or IgG4. Different classes and subclasses of immunoglobulin have different properties, which may be advantageous in different applications. For example, IgG4 antibodies have reduced binding to Fc receptors.

Naturally occurring immunoglobulins have a common core structure in which two identical light chains (about 24 kDa) and two identical heavy chains (about 55 or 70 kDa) form a tetramer. The amino-terminal portion of each chain is known as the variable (V) region and can be distinguished from the more conserved constant (C) regions of the remainder of each chain.

Most of the amino acid sequence variation in immunoglobulins is confined to three separate locations in each of the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. Proceeding from the amino-terminus, these combined regions comprised in a V region are designated FR1, CDR1, FR2, CDR2, FR3, CDR3, and FR4. The locations of CDR and FR regions and a numbering system have been defined by Kabat et al. (Kabat, E. A. et al., Sequences of Proteins of Immunological Interest, Fifth Edition, U.S. Department of Health and Human Services, U.S. Government Printing Office (1991), and updates thereof which may be found online). In addition, CDR region boundaries have been further defined by IMGT nomenclature.

A "humanized monoclonal antibody," as used herein, is an antibody which is composed of a human antibody framework, into which have been grafted complementarity determining regions (CDRs) from a non-human antibody. Changes in the human acceptor framework may also be made. Procedures for the design and production of humanized antibodies are well known in the art, and have been described, for example, in U.S. Pat. Nos. 4,816,397; 4,816,567; and 5,225,539; European Patent Application 0 120 694; European Patent Application 0 125 023; European Patent Application 0 194 276 B1; European Patent Application 0 239 400; European Patent Application 0 519 596; and International Patent Application WO 86/01533. Further details on antibodies, humanized antibodies, human engineered antibodies, and methods for their preparation can be found in Kontermann, R. and Dijbel, S. eds. (2001, 2010) Antibody Engineering, 2nd ed., Springer-Verlag, New York, NY. The entire contents of each of the patents and patent application publications listed above are incorporated herein by reference.

Variable regions of antibodies according to the described embodiments may be obtained, at least in part, by humanizing BMA031, i.e., by transferring the CDRs of BMA031 to a human framework, and further modifying one or more VL CDR to improve the stability of the binding polypeptide by reducing fragmentation of the light chain variable region. Two series of humanized BMA031 antibodies are described in PCT Publication WO 2013/037484, which is incorporated by reference herein. These two series are the HEBE1 series, comprising instant SEQ ID NOs: 5-7, 12 and 13, and the GL1BM series, comprising heavy chain variable regions as shown in instant SEQ ID NOs: 8, 15 and 16. In both cases, the light chain variable region used is as shown in instant SEQ ID NO: 14 (GL1BM VK43). The human frameworks used are IGH3-23 (instant SEQ ID NO: 17) in the case of HEBE1, and IGHV1-3*01 and IGKV3-11*01 (instant SEQ ID NOs: 18 and 19, respectively) in the case of GL1BM.

Constant regions may be derived from any human antibody constant regions. Variable region genes may be cloned into expression vectors in frame with constant region genes to express heavy and light immunoglobulin chains. Such expression vectors can be transfected into antibody producing host cells for antibody synthesis.

Human antibody variable and constant regions may be derived from sequence databases. For example, immunoglobulin sequences are available in the IMGT/LIGM database (Giudicelli et al., (2006) Nucleic Acids Res. 34 (suppl. 1): D781-D784) or VBase 30 (vbase.mrc-cpe.cam.ac.uk). Aglycosylated antibodies can have extensively modified functionality; see, Boyd et al. (1996) Mol. Immunol. 32:1311-1318. A "delta ab" or Aab modification, as used herein, is an Fc modification as described in Armour et al., (1999) Eur. J. Immunol. 29:2613-2624. Techniques for modifying glycosylation of antibody Fc regions are known in the art, and include chemical, enzymatic and/or mutational means, for example, mutation of the N297 position in the CH2 domain. Techniques for mutating antibody genes for producing aglycosylated IgG molecules are described in Tao and Morrison (1989) J. Immunol. 143:2595-2601.

Specificity, in the context of the antibodies described herein, means that the claimed antibody is capable of selectively binding its defined cognate antigen, i.e., the αβTCR/CD3 complex. The antibodies described herein bind the αβTCR/CD3 complex expressed on cells, including on T cells.

The terms "stable", "stability", and "stabilized", as used herein in the context of a binding polypeptide, refer to the resistance of the binding polypeptide to thermal and chemical degradation or fragmentation under given conditions of manufacture, preparation, transportation and storage. The "stable" compositions retain biological activity greater than or equal to 80%, 85%, 90%, 95%, 98%, 99%, 99.5%, or 99.9% under given manufacture, preparation, transportation and storage conditions. The stability of a binding polypeptide can be assessed, for example, in terms degrees of degradation or fragmentation, or levels of particular fragments or types or sizes of aggregates, compared to a control or compared to a starting material, using methods and measurements known to those skilled in the art. Such methods and measurements include, but are not limited to, reduced area under the curve (AUC), size exclusion chromatography (SEC), high performance (or high pressure) size exclusion chromatography (HPSEC), liquid chromatography-mass spectrometry (LC-MS), capillary gel electrophoresis (CGE), and sodium dodecyl sulfate polyacrylamide gel electrophoresis (SDS-PAGE), compared to a reference.

The term "nucleic acid," as used herein, includes DNA molecules which encode the antibodies described herein. Preferred DNA molecules which encode the antibodies described herein are expression vectors, which are suitable for expressing the antibody genes in a host cell. Expression vectors and host cells for antibody gene expression are known in the art; see, for example, Morrow, K. J. Genetic Engineering & Biotechnology News (Jun. 15, 2008) 28(12), and Backliwal, G. et al. (2008) Nucleic Acids Res. 36(15): e96-e96.

The terms "treat" and "treatment," as used herein, refer to the care of a patient or subject having a disease, disorder, or condition. The treatment may be directed to, but is not limited to, any one or any combination of the following: the cure of a disease, disorder, or condition; the improvement of at least one symptom of a disease, disorder, or condition; and/or a prophylactic or preventative act in which the aim is to prevent or reduce the occurrence of a disease, disorder, or condition. In certain embodiments, the treatment may be directed to, but is not limited to, the cure of a disease, disorder, or condition; or the improvement of at least one symptom of a disease, disorder, or condition.

The term "subject," as used herein, refers to any mammal, including mice, rats, gerbils, hamsters, guinea pigs, rabbits, cats, dogs, sheep, goats, pigs, cows, horses, and primates. In certain embodiments, a subject is a mammal other than a human. In certain embodiments, a subject is a non-human primate. In certain embodiments, a subject is a human.

II. Antibodies

This disclosure encompasses methods of administering one or more antigen-binding fragments of the humanized anti-αβTCR antibodies described herein to a subject in need thereof. Fragments of the antibodies are capable of binding the αβTCR/CD3 complex. They encompass Fab, Fab', F(ab')2, and F(v) fragments, or the individual light or heavy chain variable regions or any portion thereof. Fragments include, for example, Fab, Fab', F(ab')2, Fv, scFv and the like. In certain aspects, fragments lack the Fc portion of an intact antibody, clear more rapidly from the circulation, and/or can have less non-specific tissue binding than an intact antibody. In certain aspects, fragments can be produced from intact antibodies using well known methods, for example by proteolytic cleavage with enzymes such as papain (to produce Fab fragments) or pepsin (to produce F(ab')2 fragments).

In certain aspects, antibodies and/or antibody fragments encompass single-chain antibody fragments (scFv) that bind to the αβTCR/CD3 complex. In certain aspects, an scFv comprises an antibody heavy chain variable region (VH)

operably linked to an antibody light chain variable region (VL), wherein one or both of the heavy chain variable region and the light chain variable region, together or individually, form a binding site that binds αβTCR. An scFv may comprise a VH region at the amino-terminal end and a VL region at the carboxy-terminal end. Alternatively, scFv may comprise a VL region at the amino-terminal end and a VH region at the carboxy-terminal end. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). An scFv may optionally further comprise a polypeptide linker between the heavy chain variable region and the light chain variable region.

Antibodies and antibody fragments also encompass domain antibody (dAb) fragments as described in Ward, E. S. et al. (1989) Nature 341:544-546, which consist of a VH domain. Antibodies and antibody fragments also encompass heavy chain antibodies (HCAb). HCAbs are reported to form antigen-binding regions using only heavy chain variable region, in that these functional antibodies are dimers of heavy chains only (referred to as "heavy-chain antibodies" or "HCAbs"). Accordingly, in certain aspects, antibodies and antibody fragments may be HCAbs that specifically bind to the αβTCR/CD3 complex. Antibodies and antibody fragments also encompass antibodies that are small modular immunopharmaceuticals (SMIPs) or binding domain immunoglobulin fusion proteins specific for αβTCR/CD3 complex. These constructs are single-chain polypeptides comprising antigen-binding domains fused to immunoglobulin domains necessary to carry out antibody effector functions (see, WO 2005/017148). Antibodies and antibody fragments also encompass diabodies. Diabodies refer to bivalent antibodies in which VH and VL domains are expressed on a single polypeptide chain, but using a linker that is too short to allow for pairing between the two domains on the same chain. This forces the domains to pair with complementary domains of another chain and thereby creates two antigen-binding sites (see, for example, WO 93/11161). Diabodies can be bi-specific or mono-specific.

In certain aspects, an antibody or antibody fragment specifically binds to the human αβTCR/CD3 complex, i.e., such antibody or antibody fragment does not cross-react with any target other than the human αβTCR/CD3 complex.

The antibody or antibody fragment may be modified in order to increase its serum half-life, for example, by adding molecules such as PEG or other water-soluble polymers, including polysaccharide polymers and the like to increase the half-life of the antibody or antibody fragment.

Antibodies and antibody fragments may be multispecific or bispecific. For example, bispecific antibodies or antibody fragments may resemble single antibodies (or antibody fragments) that comprise two different binding sites (variable regions). Bispecific antibodies can be produced by various methods, such as chemical techniques, "polydoma" techniques or recombinant DNA techniques. Bispecific antibodies may have binding specificities for at least two different epitopes, at least one of which is the αβTCR/CD3 complex. The other specificity may be selected from any useful or desired specificity including, for example, specificity for human serum albumin for the extension of half-life in vivo.

The use of bispecific antibodies in the clinic for oncology applications is now becoming reality with the tri-functional catumaxomab (REMOVAB®) approved for use in cases of malignant ascites and the bispecific antibody blinatumomab (BLINCYTO®) approved for use used as a second-line treatment for Philadelphia chromosome-negative relapsed or refractory acute lymphoblastic leukemia (ALL). These antibodies have in common a binding arm which binds to T cells and a second arm which binds to the tumor target cell, resulting in T-cell-mediated lysis of the tumor target. Also in common, these molecules recruit T cells via the CD3 protein located on the cell surface. An alternative to recruitment via CD3 is to make use of the αs T-cell receptor (αβTCR), which is also expressed on the surface of the cell.

In certain exemplary embodiments, antibodies according to the present disclosure can be used to develop anti-tumor antibodies by combining a specificity for a tumor associated antigen with a specificity for the αs T-cell receptor (αβTCR).

III. Anti-αβTCR Antibodies

As mentioned above, two series of such humanized anti-αβTCR antibodies are described in PCT Publication WO 2013/037484, which is incorporated by reference herein. These two series are based on the murine anti-αβTCR antibody BMA031 and include the HEBE1 series, comprising SEQ ID NOs: 5-7, 12 and 13, and the GL1BM series, comprising heavy chain variable regions as shown in SEQ ID NOs: 8, 15 and 16. In both cases, the light chain variable region used is as shown in SEQ ID NO: 14 (GL1BM VK43). The human frameworks used are IGH3-23 (SEQ ID NO: 17) in the case of HEBE1, and IGHV1-3*01 (SEQ ID NO: 18) and IGKV3-11*01 (SEQ ID NO: 19) in the case of GL1BM.

In the sequences listed in Table 1, selected CDRs are shown in bold and as set forth in SEQ ID NOs: 26-28.

TABLE 1

VH, VL, and CDR amino acid sequences of exemplary anti-αβTCR antibodies.

| Antibody | Sequence | SEQ ID NO: |
|---|---|---|
| BMA031 HC VD | EVQLQQSGPELVKPGASVKMSCKASGYKFTSYVMHW VKQKPGQGLEWIGYINPYNDVTKYNEKFKGKATLTSDK SSSTAYMELSSLTSEDSAVHYCARGSYYDYDGFVYWG QGTLVTVSA | 1 |
| BMA031 LC VD | QIVLTQSPAIMSASPGEKVTMTCSATSSVSYMHWYQQK SGTSPKRWIYDTSKLASGVPARFSGSGSGTSYSLTISS MEAEDAATYYCQQWSSNPLTFGAGTKLELK | 2 |
| EUCIV3 HC VD | QVQLVQSGAEVKKPGSSVKVSCKASGYKFTSYVMHWV KQAPGQGLEWIGYINPYNDVTKYNEKFKGKATLTADES | 3 |

TABLE 1-continued

VH, VL, and CDR amino acid sequences of
exemplary anti-αβTCR antibodies.

| Antibody | Sequence | SEQ ID NO: |
|---|---|---|
| | TNTAYMELSSLRSEDTAVHYCARGSYYDYDGFVYWGQ GTLVTVSS | |
| EUCIV3 LC VD | DIQMTQSPSTLSASVGDRVTMTCSATSSVSYMHWYQQ KPGKAPKRWIYDTSKLASGVPARFIGSGSGTEFTLTISS LQPDDFATYYCQQWSSNPLTFGGGTKVEIK | 4 |
| HEBE1 HC VD | EVQLLESGGGLVQPGGSLRLSCAASGYKFTSYVMHWV KQAPGKGLEWIGYINPYNDVTKYNEKFKGKATLSRDNS KNTLYLQMNSLRAEDTAVHYCARGSYYDYDGFVYWGQ GTLVTVSS | 5 |
| HEBE1 LC VD | DIQMTQSPSTLSASVGDRVTMTCSATSSVSYMHWYQQ KPGKAPKRWIYDTSKLASGVPARFIGSGSGTEFTLTISS LQPDDFATYYCQQWSSNPLTFGGGTKVEIK | 6 |
| HEBE1 H10 HC VD | EVQLQQSGPELVKPGASVKMSCKASGYKFTSYVMHW VKQAPGKGLEWIGYINPYNDVTKYNEKFKGKATLSRDN SKNTLYLQMNSLRAEDTAVHYCARGSYYDYDGFVYWG QGTLVTVSS | 7 |
| GL1BM HC VD | QVQLVQSGAEVKKPGASVKVSCKASGYKFTSYVMHWV RQAPGQRLEWMGYINPYNDVTKYNEKFKGKATITRDTS ANTAYMELSSLRSEDTAVYYCARGSYYDYDGFVYWGQ GTLVTVSS | 8 |
| GL1BM LC VD | EIVLTQSPATLSLSPGERATLSCSATSSVSYMHWYQQK PGQAPRRWIYDTSKLASGVPARFSGSGSGTDFTLTISS LEPEDFAVYYCQQWSSNPLTFGGGTKVEIK | 9 |
| HuIgG1 Fc delta ab | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PPVAGPSVFLFPPKPKDTLMISRTPEVTCVVVDVSHED PEVKFNWYVDGVEVHNAKTKPREEQYNSTYRVVSVLT VLHQDWLNGKEYKCKVSNKGLPSSIEKTISKAKGQPRE PQVYTLPPSRDELTKNQVSLTCLVKGFYPSDIAVEWES NGQPENNYKTTPPVLDSDGSFFLYSKLTVDKSRWQQG NVFSCSVMHEALHNHYTQKSLSLSPGK | 10 |
| HuIgG4 agly Fc | ASTKGPSVFPLAPCSRSTSESTAALGCLVKDYFPEPVT VSWNSGALTSGVHTFPAVLQSSGLYSLSSVVTVPSSSL GTKTYTCNVDHKPSNTKVDKRVESKYGPPCPPCPAPE FLGGPSVFLFPPKPKDTLMISRTPEVTCVVVDVSQEDP EVQFNWYVDGVEVHNAKTKPREEQFQSTYRVVSVLTV LHQDWLNGKEYKCKVSNKGLPSSIEKTISKAKGQPREP QVYTLPPSQEEMTKNQVSLTCLVKGFYPSDIAVEWESN GQPENNYKTTPPVLDSDGSFFLYSRLTVDKSRWQEGN VFSCSVMHEALHNHYTQKSLSLSLGK | 11 |
| HEBE1 H66 HC VD | EVQLLQSGGGLVQPGGSLRLSCAASGYKFTSYVMHWV RQAPGKGLEWVGYINPYNDVTKYNEKFKGRFTLSRDN SKNTLYLQMNSLRAEDTAVYYCARGSYYDYDGFVYWG QGTLVTVSS | 12 |
| HEBE1 H71 HC VD | EVQLLESGGGLVQPGGSVRLSCAASGYKFTSYVMHWV RQAPGKGLEWVGYINPYNDVTKYNEKFKGRFTLSRDN SKNTLYLQMNSLRAEDTAVYYCARGSYYDYDGFVYWG QGTLVTVSS | 13 |
| GL1BM VK43 LC VD | EIVLTQSPATLSLSPGERATLSCSATSSVSYMHWYQQK PGQAPRRLIYDTSKLASGVPARFSGSGSGTSYTLTISSL EPEDFAVYYCQQWSSNPLTFGGGTKVEIK | 14 |
| GL1BM VH28 HC VD | QVQLVQSGAEVKKPGASVKVSCKASGYKFTSYVMHW VKQAPGQGLEWIGYINPYNDVTKYNEKFKGRVTITRDT SASTAYMELSSLRSEDTAVYYCARGSYYDYDGFVYWG QGTLVTVSS | 15 |
| GL1BM VH31 HC VD | QVQLVQSGAEVKKPGASVKVSCKASGYKFTSYVMHW VRQAPGQGLEWIGYINPYNDVTKYNEKFKGRVTITRDT SASTAYMELSSLRSEDTAVYYCARGSYYDYDGFVYWG QGTLVTVSS | 16 |

TABLE 1-continued

VH, VL, and CDR amino acid sequences of exemplary anti-αβTCR antibodies.

| Antibody | Sequence | SEQ ID NO: |
|---|---|---|
| IGH3-23 HC | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK | 17 |
| IGHV1-3*01 HC | QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAR | 18 |
| IGKV3-11*01 LC VD | EIVLTQSPATLSLSPGERATLSCRASQSVSSYLAWYQQKPGQAPRLLIYDASNRATGIPARFSGSGSGTDFTLTISSLEPEDFAVYYCQQRSNWP | 19 |
| GL1BM VHΔS | QVQLVQSGAEVKKPGASVKVSCKASGYKFTSYVMHWVRQAPGQRLEWMGYINPYNDVTKYNEKFKGKATITRDTSASTAYMELSSLRSEDTAVYYCARGSYYDYDGFVYWGQGTLVTVSS | 20 |
| GL1BM VK1 | EIVLTQSPATLSLSPGERATLSCSATSSVSYMHWYQQKPGQAPRRWIYDTSKLASGVPARFSGSGSGTDFTLTISSLEPEDFAVYYCQQWSSNPLTFGGGTKVEIK | 21 |
| GL1BM VK27 | EIVLTQSPATLSLSPGERATLSCSATSSVSYMHWYQQKPGQAPRRWIYDTSKLASGVPARFSGSGSGTDFTLTISSMEPEDFAVYYCQQWSSNPLTFGGGTKVEIK | 22 |
| GL1BM VHΔS VH11 | QVQLVQSGAEVKKPGASVKVSCKASGYKFTSYVMHWVKQKPGQGLEWIGYINPYNDVTKYNEKFKGKATITRDTSASTAYMELSSLRSEDTAVYYCARGSYYDYDGFVYWGQGTLVTVSS | 23 |
| GL1BM VHΔS VH15 | QVQLVQSGAEVKKPGASVKVSCKASGYKFTSYVMHWVKQAPGQGLEWIGYINPYNDVTKYNEKFKGKATITRDTSASTAYMELSSLRSEDTAVYYCARGSYYDYDGFVYWGQGTLVTVSS | 24 |
| VH31 LC | EIVLTQSPATLSLSPGERATLSCSATSSVSYMHWYQQKPGQAPRRLIYDTSKLASGVPARFSGSGSGTSYTLTISSLEPEDFAVYYCQQWSSNPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 25 |
| GL1BM VK43 LCDR1 | S-A-T-S-S-V-S-Y-M-H | 26 |
| GL1BM VK43 LCDR2 | D-T-S-K-L-A-S | 27 |
| Stabilized GL1BM VK43 LCDR3 | Q-Q-W-S-S-$X_1$-$X_2$-L-T, wherein $X_1$ is Q, D, H, S, Y, or A; and $X_2$ is P or A | 28 |

Comparison of LCDR3 of GL1BM VK43 (QQWSSNPLT (SEQ ID NO: 29)) in SEQ ID NO:14 to LCDR3 of stabilized GL1BM VK43 (Q-Q-W-S-S-$X_1$-$X_2$-L-T, wherein $X_1$ is Q, D, H, S, Y, or A, and $X_2$ is P or A (SEQ ID NO: 28)) reveals that amino acids $X_1$ and $X_2$ in SEQ ID NO: 28 correspond to N and P, respectively, in SEQ ID NO: 29.

In certain embodiments, there is provided a binding polypeptide that specifically binds human αβTCR/CD3 complex, comprising a heavy chain variable region, a light chain variable region, and a constant region, wherein:
 the light chain variable region comprises three complementarity determining regions (CDRs) LCDR1, LCDR2, and LCDR3 comprising the amino acid sequences set forth in SEQ ID NOs: 26, 27, and 28, respectively;
 SEQ ID NO: 28 comprises the amino acid sequence Q-Q-W-S-S-$X_1$-$X_2$-L-T, wherein $X_1$ is an amino acid selected from the group consisting of Q, D, H, S, Y, and A, and $X_2$ is an amino acid selected from the group consisting of P and A; and
 the constant region is of human origin.
In certain embodiments, $X_1$ is Q.
In certain embodiments, $X_1$ is D.
In certain embodiments, $X_1$ is H.
In certain embodiments, $X_1$ is S.
In certain embodiments, $X_1$ is Y.
In certain embodiments, $X_1$ is A.
In certain embodiments, $X_2$ is P.
In certain embodiments, $X_2$ is A.
In certain embodiments, $X_1$ is Q, and $X_2$ is P.
In certain embodiments, $X_1$ is Q, and $X_2$ is A.
In certain embodiments, $X_1$ is D, and $X_2$ is P.
In certain embodiments, $X_1$ is D, and $X_2$ is A.
In certain embodiments, $X_1$ is H, and $X_2$ is P.

In certain embodiments, $X_1$ is H, and $X_2$ is A.
In certain embodiments, $X_1$ is S, and $X_2$ is P.
In certain embodiments, $X_1$ is S, and $X_2$ is A.
In certain embodiments, $X_1$ is Y, and $X_2$ is P.
In certain embodiments, $X_1$ is Y, and $X_2$ is A.
In certain embodiments, $X_1$ is A, and $X_2$ is P.
In certain embodiments, $X_1$ is A, and $X_2$ is A.

In certain embodiments, the light chain variable region further comprises a human light chain framework region in accordance with SEQ ID NO: 14.

In certain embodiments, the binding polypeptide has increased stability at pH greater than 5.0 compared to reference antibody VH31.

In certain embodiments, the binding polypeptide has increased stability at a temperature greater than 4° C. compared to reference antibody VH31.

In certain embodiments, the heavy chain variable region comprises an amino acid sequence selected from the group consisting of SEQ ID NOs: 7, 12, 13, 15, and 16.

In certain embodiments, the heavy chain variable region comprises an amino acid sequence selected from the group consisting of SEQ ID NO: 7, SEQ ID NO: 12, and SEQ ID NO: 13.

In certain embodiments, the heavy chain variable region comprises an amino acid sequence selected from the group consisting of SEQ ID NO: 15 and SEQ ID NO: 16.

In certain embodiments, the heavy chain variable region comprises the amino acid sequence set forth as SEQ ID NO: 15.

In certain embodiments, the heavy chain variable region comprises the amino acid sequence set forth as SEQ ID NO: 16.

IV. Modified Anti-αβTCR Antibodies

Anti-αβTCR antibodies may comprise one or more modifications. Modified anti-αβTCR antibodies according to the invention can be made using any techniques known in the art.

i) Reducing Fragmentation

The term "fragmentation" as used herein in the context of a binding polypeptide composition refers to cleavage of the binding polypeptide or a first portion thereof into two or more portions each of lower molecular weight than the original binding polypeptide or first portion thereof. Such fragmentation forms include, but are not limited to, a full-length unpaired heavy chain, a full-length unpaired light chain, a first full-length heavy chain paired with a second full-length heavy chain, a full-length heavy chain paired with a partial heavy chain, a first partial heavy chain paired with a second partial heavy chain, a full-length heavy chain paired with a full-length light chain, a full-length heavy chain paired with a partial light chain, a partial heavy chain paired with a full-length light chain, a partial heavy chain paired with a partial light chain, a first full-length heavy chain paired with a second full-length heavy chain and a full-length light chain, a first full-length heavy chain paired with a second full-length heavy chain and a partial light chain, a first full-length heavy chain paired with a first partial light chain and with a second full-length heavy chain paired with a second partial light chain, a first full-length heavy chain paired with partial heavy chain and a full-length light chain, a first full-length heavy chain paired with partial heavy chain and two full-length light chains, a first full-length heavy chain paired with a partial heavy chain and a partial light chain, a first partial heavy chain paired with a second partial heavy chain and a full-length light chain, and a first partial heavy chain paired with a second partial heavy chain and a partial light chain.

As used herein, a "fragment" refers to at least one amino acid. Typically, a fragment will comprise two or more amino acids linked together, more typically at least 10, 20, 30, 40, or 50 such amino acids. Particularly for fragments comprising more than one polypeptide chain, a fragment can comprise, for example, at least 100, at least 200, at least 300, at least 400, at least 500, at least 600, or at least 700 amino acids.

Fragmentation may be caused by a variety of mechanisms, e.g., due to the disruption of native covalent bonds, resulting in the cleavage of polypeptide backbones through spontaneous (e.g., non-enzymatic) or enzymatic reactions. In general, protein backbones are highly stable under physiological conditions.

However, specific regions and motifs may be more susceptible to fragmentation due to their amino acid sequence, the flexibility of the two- or three-dimensional polypeptide structure, and incompatible solvent and environmental conditions (e.g., temperature and pH).

For example, it has been shown that amino acids Asp (D), Gly (G), Ser (S), Thr (T), Cys (C), and Asn (N) are particularly susceptible to cleavage in the polypeptide backbone of antibodies. See, e.g., Liu H., et al. J. Am. Soc. Mass Spectrom. 2009; 20: 2258-2264. In addition, the Asn-Pro (N-P) amide bond is known to undergo complete cleavage in the presence of ammonia. See, e.g., Tarelli E. and Corran P. H. J. Peptide Res. 2003; 62: 245-251.

Fragmentation may occur at any step during the manufacture or storage of biologic compositions. Because fragmentation may result in reduced potency or the presence of unwanted and potentially immunogenic species, reducing fragmentation is a key consideration in the production of any biologic therapeutic.

In some embodiments, less than 5% (e.g., less than 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1%) of the antibody is fragmented after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C.

Methods for determining the amount of monomeric binding polypeptide, as well as the amount of monomeric, oligomeric, aggregated, or fragmented forms of the binding polypeptide present in solution are described herein and exemplified in the working examples. For example, a skilled artisan can determine the percentage of whole, fragmented, unfolded intermediates, and/or aggregated species present in a given solution using, e.g., size exclusion chromatography high-performance liquid chromatography (SEC-HPLC), static light scattering (SLS), Fourier transform infrared spectroscopy (FTIR), circular dichroism (CD), urea-induced protein unfolding techniques, intrinsic tryptophan fluorescence, non-reducing sodium dodecyl sulfate polyacrylamide gel electrophoresis (SDS-PAGE), and differential scanning calorimetry (DSC). In the working examples described herein, the inventors exemplify the use of, among others, SEC-HPLC and SDS-PAGE to determine the physical state of the binding polypeptides in solution.

ii) Reducing Immunogenicity

In certain exemplary embodiments, de-immunization can be used to decrease the immunogenicity of and antibody, or antigen binding portion thereof. As used herein, the term "de-immunization" includes alteration of an antibody, or antigen binding portion thereof, to modify one or more T-cell epitopes (see, e.g., WO 98/52976 A1, WO 00/34317 A2). For example, VH and VL sequences from the starting antibody may be analyzed and a human T-cell epitope "map" may be generated from each V region showing the location of epitopes in relation to complementarity-determining regions (CDRs) and other key residues within the sequence. Individual T-cell epitopes from the T-cell epitope map can be analyzed in order to identify alternative amino acid substitutions with a low risk of altering activity of the final antibody. A range of alternative VH and VL sequences can be designed comprising combinations of amino acid substitutions, and these sequences can be subsequently incorporated into a range of anti-αβTCR antibodies or anti-αβTCR antibody fragments for use in the methods disclosed herein, which are then tested for function. Complete heavy and light chain genes comprising modified V and human C regions can then be cloned into expression vectors and the subsequent plasmids can be introduced into cell lines for the production of whole antibody. The antibodies can then be compared in appropriate biochemical and biological assays, and the optimal variant can be identified.

iii) Effector Functions and Fc Modifications

A humanized monoclonal antibody, or a humanized monoclonal antibody fragment (e.g., an anti-αβTCR antibody or fragment thereof) may comprise an antibody constant region (e.g., an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors, i.e., Fcγ receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer, and control of immunoglobulin production.

In certain embodiments, a humanized monoclonal antibody, or a humanized monoclonal antibody fragment (e.g., an anti-αβTCR antibody or fragment thereof), binds to an Fcγ receptor. In alternative embodiments, a humanized monoclonal antibody, or a humanized monoclonal antibody fragment (e.g., an anti-αβTCR antibody or fragment thereof) may comprise a constant region which is incapable of directing one or more effector functions (e.g., ADCC activity) and/or is unable to bind Fcγ receptor.

Certain embodiments described herein provide a humanized monoclonal antibody, or a humanized monoclonal antibody fragment (e.g., an anti-αβTCR antibody or fragment thereof) in which at least one amino acid in one or more of the constant region domains has been deleted or otherwise altered so as to provide desired biochemical characteristics such as, e.g., reduced or enhanced effector functions, the ability to non-covalently dimerize, increased ability to localize at the site of a tumor, reduced serum half-life, and/or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, a humanized monoclonal antibody, or a humanized monoclonal antibody fragment (e.g., an anti-αβTCR antibody or fragment thereof), comprises constant regions derived from different antibody isotypes (e.g., constant regions from two or more of a human IgG1, IgG2, IgG3, or IgG4). In other embodiments, a humanized monoclonal antibody, or a humanized monoclonal antibody fragment (e.g., an anti-αβTCR antibody or fragment thereof) comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, a humanized monoclonal antibody, or a humanized monoclonal antibody fragment (e.g., an anti-αβTCR antibody or fragment thereof) comprises an Fc region or portion thereof from a human IgG4 molecule and a Ser228Pro (S228P) mutation (EU numbering) in the core hinge region of the molecule.

In certain exemplary embodiments, the Fc portion of a humanized monoclonal antibody, or a humanized monoclonal antibody fragment (e.g., an anti-αβTCR antibody or fragment thereof) may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases, it may be that constant region modifications consistent with the instant disclosure moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, bio-distribution and serum half-life, may easily be measured and quantified using well know immunological techniques without undue experimentation.

In certain embodiments, an Fc domain employed in a humanized monoclonal antibody, or a humanized monoclonal antibody fragment (e.g., an anti-αβTCR antibody or fragment thereof) is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The antibodies may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein.

In one exemplary embodiment, a humanized monoclonal antibody, or a humanized monoclonal antibody fragment (e.g., an anti-αβTCR antibody or fragment thereof) may comprise an Fc variant comprising an amino acid substitution at EU position 268 (e.g., H268D or H268E). In another exemplary embodiment, a humanized monoclonal antibody, or a humanized monoclonal antibody fragment (e.g., an anti-αβTCR antibody or fragment thereof) may comprise an amino acid substitution at EU position 239 (e.g., S239D or S239E) and/or EU position 332 (e.g., I332D or I332Q).

In certain embodiments, a humanized monoclonal antibody, or a humanized monoclonal antibody fragment (e.g., an anti-αβTCR antibody or fragment thereof) may comprise an Fc variant comprising an amino acid substitution which alters the antigen-independent effector functions of the antibody, in particular the circulating half-life of the antibody. Such antibodies exhibit either increased or decreased binding to neonatal Fc receptor (FcRn) when compared to antibodies lacking these substitutions, and therefore have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g., for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered antibodies exhibit reduced transport across the epithelium of kidney glomeruli from the vasculature. In another embodiment, the altered antibodies exhibit reduced transport across the blood brain barrier (BBB) from the brain, into the vascular space.

In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein in its entirety for all purposes. In certain exemplary embodiments, a humanized monoclonal antibody, or a humanized monoclonal antibody fragment (e.g., an anti-αβTCR antibody or fragment thereof) comprises an Fc domain having one or more of the following substitutions: V284E, H285E, N286D, K290E and S304D (EU numbering).

In other embodiments, a humanized monoclonal antibody, or a humanized monoclonal antibody fragment (e.g., an anti-αβTCR antibody or fragment thereof) for use in the diagnostic and treatment methods described herein has a constant region, e.g., an IgG1 or IgG4 heavy chain constant region, which is altered to reduce or eliminate glycosylation. For example, an antibody may also comprise an Fc variant comprising an amino acid substitution which alters the glycosylation of the antibody. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduced or altered glycosylation are disclosed in International PCT Publication No. WO05/018572, which is incorporated by reference herein in its entirety for all purposes. In certain embodiments, the antibodies, or fragments thereof, are modified to eliminate glycosylation. Such antibodies, or fragments thereof, may be referred to as "agly" antibodies, or fragments thereof (e.g., "agly" antibody fragments). While not intending to be bound by scientific theory, it is believed that agly antibodies, or fragments thereof, may have an improved safety and stability profile in vivo. Exemplary agly antibodies, or agly antibody fragments, comprise an aglycosylated Fc region of an IgG4 antibody which is devoid of Fc-effector function thereby eliminating the potential for Fc-mediated toxicity to normal vital organs. In yet other embodiments, agly antibodies, or agly antibody fragments, comprise an altered glycan. For example, the agly antibody or agly antibody fragment may have a reduced number of fucose residues on an N-glycan at Asn297 (N297) of the Fc region, i.e., is afucosylated. In another embodiment, the agly antibody or agly antibody fragment may have an altered number of sialic acid residues on the N-glycan at Asn297 of the Fc region.

iv) Covalent Attachment

A humanized monoclonal antibody, or a humanized monoclonal antibody fragment (e.g., an anti-αβTCR antibody or fragment thereof) may be modified, e.g., by the covalent attachment of a molecule to the antibody such that the covalent attachment does not prevent the antibody from specifically binding to its cognate epitope. For example, but not by way of limitation, a humanized monoclonal antibody, or a humanized monoclonal antibody fragment (e.g., an anti-αβTCR antibody or fragment thereof), may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, and the like. Additionally, the derivative may contain one or more non-classical amino acids.

A humanized monoclonal antibody, or a humanized monoclonal antibody fragment (e.g., an anti-αβTCR antibody or fragment thereof) may further be recombinantly fused to a heterologous polypeptide at the N- or C-terminus or chemically conjugated (including covalent and non-covalent conjugations) to polypeptides or other compositions. For example, anti-αβTCR antibodies may be recombinantly fused or conjugated to molecules useful as labels in detection assays and effector molecules such as heterologous polypeptides, drugs, radionuclides, or toxins. See, e.g., PCT publications WO 92/08495, WO 91/14438, and WO 89/12624; U.S. Pat. No. 5,314,995; and EP 396,387.

A humanized monoclonal antibody, or a humanized monoclonal antibody fragment (e.g., an anti-αβTCR antibody or fragment thereof) may be fused to one or more heterologous polypeptides to increase the in vivo half-life or for use in immunoassays using methods known in the art. For example, in one embodiment, polyethylene glycol (PEG) can be conjugated to a humanized monoclonal antibody, or a humanized monoclonal antibody fragment (e.g., an anti-αβTCR antibody or fragment thereof) to increase its half-life in vivo. Leong, S. R., et al., Cytokine 16:106 (2001); Chapman A. P, Adv. Drug Deliv. Rev. 54:531 (2002); or Weir et al., Biochem. Soc. Transactions 30:512 (2002).

Moreover, a humanized monoclonal antibody, or a humanized monoclonal antibody fragment (e.g., an anti-αβTCR antibody or fragment thereof) can be fused to one or more marker sequences, such as a peptide, to facilitate purification or detection of the humanized monoclonal antibody, or humanized monoclonal antibody fragment (e.g., an anti-αβTCR antibody or fragment thereof). In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767-778 (1984)) and the "flag" tag.

A humanized monoclonal antibody, or a humanized monoclonal antibody fragment (e.g., an anti-αβTCR antibody or fragment thereof) may be used in non-conjugated form or may be conjugated to at least one of a variety of molecules, e.g., to improve the therapeutic properties of the molecule, to facilitate target detection, or for imaging or therapy of the subject. A humanized monoclonal antibody, or a humanized monoclonal antibody fragment (e.g., an anti-αβTCR antibody or fragment thereof) can be labeled or conjugated either before or after purification, when purification is performed. In particular, a humanized monoclonal antibody, or a humanized monoclonal antibody fragment (e.g., an anti-αβTCR antibody or fragment thereof) may be conjugated to therapeutic agents, prodrugs, peptides, proteins, enzymes, viruses, lipids, biological response modifiers, pharmaceutical agents, or PEG.

The present disclosure further encompasses a humanized monoclonal antibody, or a humanized monoclonal antibody fragment (e.g., an anti-αβTCR antibody or fragment thereof) conjugated to a diagnostic or therapeutic agent. A humanized monoclonal antibody, or a humanized monoclonal antibody fragment (e.g., an anti-αβTCR antibody or fragment thereof) can be used diagnostically to, for example, monitor the development or progression of an immune cell disorder (e.g., CLL) as part of a clinical testing procedure to, e.g., determine the efficacy of a given treatment and/or prevention regimen. Detection can be facilitated by coupling a humanized monoclonal antibody, or a humanized monoclonal antibody fragment (e.g., an anti-αβTCR antibody or fragment thereof) to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present disclosure. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, and aequorin; and examples of suitable radioactive material include $^{125}$I, $^{131}$I, $^{111}$In and $^{99}$Tc.

A humanized monoclonal antibody, or a humanized monoclonal antibody fragment (e.g., an anti-αβTCR antibody or fragment thereof) for use in the diagnostic and treatment methods disclosed herein may be conjugated to one or more cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, a humanized monoclonal antibody, or a humanized monoclonal antibody fragment (e.g., an anti-αβTCR antibody or fragment thereof) for use in the diagnostic and treatment methods disclosed herein can be conjugated to a molecule that decreases tumor cell growth. In other embodiments, the disclosed compositions may comprise a humanized monoclonal antibody, or a humanized monoclonal antibody fragment (e.g., an anti-αβTCR antibody or fragment thereof) coupled to drugs or prodrugs. Still other embodiments described herein comprise the use of antibodies, or fragments thereof, conjugated to specific biotoxins or their cytotoxic fragments such as ricin, gelonin, *Pseudomonas* exotoxin or diphtheria toxin or the like. The selection of which conjugated or unconjugated antibody to use will depend on the type and stage of cancer, use of adjunct treatment (e.g., chemotherapy or external radiation)

and subject condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include, but are not limited to: $^{67}$Cu, $^{67}$Ga, $^{90}$Y, $^{105}$Rh, $^{111}$In, $^{123}$I, $^{125}$I, $^{131}$I, $^{153}$Sm, $^{166}$Ho, $^{177}$Lu, $^{186}$Re, and $^{186}$Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

V. Antibody Production

Antibody production can be performed by any technique known in the art, including in transgenic organisms such as goats (see, Pollock et al. (1999) J. Immunol. Methods 231:147-157), chickens (see, Morrow, K. J. J. (2000) Genet. Eng. News 20:1-55), mice (see Pollock et al., supra) or plants (see, Doran, P. M. (2000) Curr. Opinion Biotechnol. 11:199-204; Ma. J. K-C. (1998) Nat. Med. 4:601-606; Baez, J. et al. (2000) BioPharm. 13:50-54; Stoger, E. et al. (2000) Plant Mol. Biol. 42:583-590). Antibodies may also be produced by chemical synthesis or by expression of genes encoding the antibodies in host cells.

A polynucleotide encoding a humanized monoclonal antibody, or a humanized monoclonal antibody fragment (e.g., an anti-αβTCR antibody or fragment thereof) is isolated and inserted into a replicable construct or vector such as a plasmid for further propagation or expression in a host cell. Constructs or vectors (e.g., expression vectors) suitable for the expression of a humanized monoclonal antibody, or a humanized monoclonal antibody fragment (e.g., an anti-αβTCR antibody or fragment thereof) according to the described embodiments are available in the art. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin can be produced and maintained in culture. A single vector or multiple vectors can be used for the expression of a humanized immunoglobulin.

Polynucleotides encoding a humanized monoclonal antibody, or a humanized monoclonal antibody fragment (e.g., an anti-αβTCR antibody or fragment thereof) are readily isolated and sequenced using conventional procedures (e.g., oligonucleotide probes). Vectors that may be used include plasmid, virus, phage, transposons, minichromosomes of which plasmids are a typical embodiment. Generally, such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired, both the heavy chain and light chain can be inserted into the same vector prior to such introduction.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3, T7 promoters for E. coli; 3-phosphoglycerate kinase or other glycolytic enzymes e.g., enolase, glyceraldehyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, Rous sarcoma virus (RSV) promoter and the early or late Simian virus 40 and non-viral promoters such as EF-1 alpha (Mizushima and Nagata (1990) Nucleic Acids Res. 18(17):5322). Those of skill in the art will be able to select the appropriate promoter for expressing a humanized antibody or portion thereof.

Where appropriate, e.g., for expression in cells of higher eukaryotes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, WO 04/09823). Whilst such enhancers are often located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), tet gene (tetracycline resistance) and eukaryotic cells (e.g., neomycin (G418 or geneticin), gpt (mycophenolic acid), ampicillin, or hygromycin 5 resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody described herein. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polyadenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification. The codon usage of the antibodies described herein can be modified to accommodate codon bias of the host cell such to augment transcript and/or product yield (e.g., Hoekema, A. et al. (1987) Mol. Cell Biol. 7(8):2914-24). The choice of codons may be based upon compatibility with the host cell used for expression.

This disclosure thus relates to isolated nucleic acid molecules that encode the humanized immunoglobulins, or heavy or light chains, thereof. This disclosure also relates to isolated nucleic acid molecules that encode an antigen-binding portion of the immunoglobulins and their chains.

A humanized monoclonal antibody, or a humanized monoclonal antibody fragment (e.g., an anti-αβTCR antibody or fragment thereof) can be produced, for example, by the expression of one or more recombinant nucleic acids encoding the antibody in a suitable host cell. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Host cells can be prokaryotic, including bacterial cells such as $E.$ $coli$ (e.g., strain DH5α™) (Invitrogen, Carlsbad, CA), PerC6 (Crucell, Leiden, NL), $B.$ $subtilis$ and/or other suitable bacteria; eukaryotic cells, such as fungal or yeast cells (e.g., $Pichia$ $pastoris, Aspergillus$ sp., $Saccharomyces$ $cerevisiae,$ $Schizosaccharomyces$ $pombe,$ $Neurospora$ $crassa$), or other lower eukaryotic cells, and cells of higher eukaryotes such as those from insects (e.g., $Drosophila$ Schnieder S2 cells, Sf9 insect cells) (WO 94/126087), BTI-TN-5B1-4 (High Five™) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L. A. (1980) Proc. Natl. Acad. Sci. USA, 77(7):4216-4220), 293 (ATCC Accession No. CRL-1573), HEK, HeLa (ATCC Accession No. CCL-2), CVI (ATCC Accession No. CCL-70), WOP (Dailey, L., et al. (1985) J. Virol., 54:739-749), 3T3, 293T (Pear, W. S., et al. (1993) Proc. Natl. Acad. Sci. U.S.A., 90:8392-8396), NS0 cells, SP2/0 cells, HuT 78 cells, and the like, or plants (e.g., tobacco, lemna (duckweed), and algae). See, for example, Ausubel, F. M. et al., eds. Current Protocols in Molecular Biology, Greene Publishing Associates and John Wiley & Sons Inc. (1993). In some embodiments, the host cell is not part of a multicellular organism (e.g., plant or animal), e.g., it is an isolated host cell or is part of a cell culture.

Host cells may be cultured in spinner flasks, shake flasks, roller bottles, wave reactors (e.g., System 1000 from wavebiotech.com) or hollow fiber systems, but it is preferred for large scale production that stirred tank reactors or bag reactors (e.g., Wave Biotech, Somerset, New Jersey USA) are used particularly for suspension cultures. Stirred tank reactors can be adapted for aeration using e.g., spargers, baffles or low shear impellers. For bubble columns and airlift reactors, direct aeration with air or oxygen bubbles maybe used. Where the host cells are cultured in a serum-free culture medium, the medium can be supplemented with a cell protective agent such as pluronic F-68 to help prevent cell damage as a result of the aeration process. Depending on the host cell characteristics, microcarriers may be used as growth substrates for anchorage dependent cell lines, or the cells may be adapted to suspension culture. The culturing of host cells, particularly vertebrate host cells, may utilize a variety of operational modes such as batch, fed-batch, repeated batch processing (see, Drapeau et al. (1994) Cytotechnology 15:103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al. (1995) Cytotechnology 17:153-163, or commercially available media such as ProCHO™ or UltraCHO™ (Cambrex NJ, USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) Animal Cell Technology: Developments Towards the 21st Century (Beuvery, E. C. et al., eds), pp. 619-623, Kluwer Academic publishers).

A humanized monoclonal antibody, or a humanized monoclonal antibody fragment (e.g., an anti-αβTCR antibody or fragment thereof) according to the described embodiments may be secreted into the medium and recovered and purified therefrom using a variety of techniques to provide a degree of purification suitable for the intended use. For example, the use of a humanized monoclonal antibody, or a humanized monoclonal antibody fragment (e.g., an anti-αβTCR antibody or fragment thereof) for the treatment of human subjects typically mandates at least 95% purity as determined by reducing SDS-PAGE, more typically 98% or 99% purity, when compared to the culture media comprising the therapeutic antibodies. In the first instance, cell debris from the culture media can be removed using centrifugation followed by a clarification step of the supernatant using e.g., microfiltration, ultrafiltration and/or depth filtration. Alternatively, a humanized monoclonal antibody, or a humanized monoclonal antibody fragment (e.g., an anti-αβTCR antibody or fragment thereof) can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see, U.S. Pat. No. 5,429,746) are available. In one embodiment, a humanized monoclonal antibody, or a humanized monoclonal antibody fragment (e.g., an anti-αβTCR antibody or fragment thereof), following various clarification steps, are captured using Protein A or Protein G affinity chromatography followed by further chromatography steps such as ion exchange and/or HA chromatography, anion or cation exchange, size exclusion chromatography and ammonium sulphate precipitation. Various virus removal steps may also be employed (e.g., nanofiltration using, e.g., a DV-20 filter). Following these various steps, a purified preparation comprising at least 10 mg/mL or greater, e.g., 100 mg/mL or greater of the antibody described herein is provided and, therefore, forms another embodiment described herein. Concentration to 100 mg/mL or greater can be generated by ultracentrifugation. Such preparations are substantially free of aggregated forms of antibodies described herein.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see, Sanchez et al. (1999) J. Biotechnol. 72:13-20; Cupit, P. M. et al. (1999) Lett. Appl. Microbiol. 29:273-277.

The present disclosure also relates to cells comprising a nucleic acid, e.g., a vector, described herein (e.g., an expression vector). For example, a nucleic acid (i.e., one or more nucleic acids) encoding the heavy and light chains of a humanized immunoglobulin according to the described embodiments, or a construct (e.g., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanized antibody can be isolated, for example, from the host cells, culture medium, or milk. This process encompasses expression in a host cell (e.g., a mammary gland cell) of a transgenic animal or plant (e.g., tobacco) (see, e.g., WO 92/03918).

VI. Methods of Treating or Preventing T-Cell-Mediated Disorders

Suppression of T-cell activity is desirable in a number of situations in which immunosuppression is warranted, and/or an autoimmune condition occurs. Accordingly, targeting of the αβTCR/CD3 complex is indicated in the treatment of diseases involving an inappropriate or undesired immune response, such as inflammation, autoimmunity, and/or other conditions involving such mechanisms. In one embodiment, such disease or disorder is an autoimmune and/or inflammatory disease. Examples of such autoimmune and/or inflammatory T-cell mediated diseases include but are not limited to: systemic lupus erythematosus (SLE), rheumatoid arthritis (RA), inflammatory bowel disease (IBD) (including ulcerative colitis (UC) and Crohn's disease (CD)), multiple sclerosis (MS), scleroderma, type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjögren's syndrome, Guillain-Barré syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, Behcet's disease, primary biliary cirrhosis, uveitis, myocarditis, rheumatic fever, ankylosing spondylitis, glomerulonephritis, sarcoidosis, dermatomyositis, myasthenia gravis, polymyositis, alopecia areata, and vitilgo.

In one embodiment, such disease or disorder is SLE. In one embodiment, such disease or disorder is RA. In one embodiment, such disease or disorder is IBD. In one embodiment, such disease or disorder is MS. In one embodiment, such disease or disorder is T1D.

In another embodiment, such disease or disorder is a xenotransplant, an allotransplant, a xenopregnancy, preeclampsia, or Rh disease.

In specific embodiments, the antibodies according to the described embodiments are used to aid transplantation by immunosuppressing the subject. Such use alleviates graft-versus-host disease (GvHD), a common complication following xenograft or allograft (including, but not limited to: the transplant of stem cells, bone marrow, tissues, body parts, and solid organs). Tissues may include, but are not limited to: cornea, sclera, bone, skin, blood vessels, and heart valves. Body parts may include, but are not limited to: a face or a portion thereof, one or more arms or portions thereof, one or more hands or portions thereof, one or more legs or portions thereof, and a scalp or portions thereof. Solid organs may include, but are not limited to: heart, lung, liver, kidney, pancreas, stomach, small intestine, large intestine, testis and ovary. For a description of existing treatments for graft-versus-host disease, see, e.g., Svennilson, Bone Marrow Transplantation (2005) 35:S65-S67, and references cited therein. Advantageously, the antibodies presented in this disclosure may be used in combination with other available therapies.

With regard to the treatment of autoimmune diseases, combination therapy may include administration of an antibody described herein together with a medicament, which together with the antibody comprises an effective amount for preventing or treating such autoimmune diseases. Where said autoimmune disease is Type 1 diabetes, the combination therapy may encompass one or more of an agent that promotes the growth of pancreatic beta-cells or enhances beta-cell transplantation, such as beta cell growth or survival factors or immunomodulatory antibodies. Where said autoimmune disease is rheumatoid arthritis, said combination therapy may encompass one or more of methotrexate, an anti-TNF-α antibody, a TNF-α receptor-Ig fusion protein, an anti-IL-15 or anti-IL-21 antibody, a non-steroidal anti-inflammatory drug (NSAID), or a disease-modifying anti-rheumatic drug (DMARD). For example, the additional agent may be a biological agent such as an anti-TNF agent (e.g., ENBREL®, infliximab (REMICADE®) and adalimumab (HUMIRA®) or rituximab (RITUXAN®). Where said autoimmune disease is hematopoietic transplant rejection, hematopoietic growth factor(s) (such as erythropoietin, G-CSF, GM-CSF, IL-3, IL-11, thrombopoietin, etc.) or antimicrobial(s) (such as antibacterial, antiviral, antifungal drugs) may be administered. Where said autoimmune disease is psoriasis, the additional agent may be one or more of tar and derivatives thereof, phototherapy, corticosteroids, cyclosporine A, vitamin D analogs, methotrexate, p38 mitogen-activated protein kinase (MAPK) inhibitors, as well as biologic agents such as anti-TNF-α agents and RITUXAN®. Where said autoimmune disease is an inflammatory bowel disease (IBD) such as, for example, Crohn's disease or ulcerative colitis, the additional agent may be one or more of aminosalicylates, corticosteroids, immunomodulators, antibiotics, or biologic agents such as REMICADE® and HUMIRA®.

The combination treatment may be carried out in any way as deemed necessary or convenient by the person skilled in the art and for the purpose of this specification, no limitations with regard to the order, amount, repetition or relative amount of the compounds to be used in combination is contemplated. Accordingly, the antibodies according to the described embodiments may be formulated into pharmaceutical compositions for use in therapy.

VII. Pharmaceutical Compositions and Methods of Administration of Anti-αβTCR Antibodies In certain embodiments, pharmaceutical compositions comprising a humanized monoclonal antibody, or a humanized monoclonal antibody fragment (e.g., an anti-αβTCR antibody or fragment thereof) described herein, or a ligand or ligands identifiable by an assay method as defined in the previous aspect of the disclosure are provided. Ligands may be immunoglobulins, peptides, nucleic acids or small molecules, as discussed herein. They are referred to, in the following discussion, as "compounds."

A pharmaceutical composition described herein is a composition of matter comprising a compound or compounds capable of modulating T-cell activity as an active ingredient. The compound is in the form of any pharmaceutically acceptable salt, or e.g., where appropriate, is an analog, free base form, tautomer, enantiomer racemate, or combination thereof. The active ingredients of a pharmaceutical composition comprising the active ingredient described herein are contemplated to exhibit therapeutic activity, for example, in the treatment of graft-versus-host disease, when administered in an amount which depends on the particular case.

In certain embodiments, a pharmaceutical composition comprises a humanized monoclonal antibody, or a humanized monoclonal antibody fragment (e.g., an anti-αβTCR antibody or fragment thereof) described herein, and pharmaceutically acceptable carrier or diluent.

In certain embodiments, one or more compounds described in this disclosure may be used in combination with any art recognized compound known to be suitable for treating the particular indication in treating any of the aforementioned conditions. Accordingly, one or more compounds described herein may be combined with one or more art recognized compounds known to be suitable for treating the foregoing indications such that a convenient, single composition can be administered to the subject. Dosage regimens may be adjusted to provide the optimum therapeutic response.

For example, several divided doses may be administered daily or the dose may be proportionally reduced as indicated by the exigencies of the therapeutic situation.

The active ingredient may be administered in a convenient manner such as by the oral, intravenous (where water soluble), intramuscular, subcutaneous, intranasal, intradermal or suppository routes or implanting (e.g., using slow release molecules). In the case of a transplant, the active ingredient may also be used to treat cells, tissues, or organs being transplanted into a patient prior to the transplantation. This may be done in order to prevent, decrease the likelihood, or lessen the symptoms of, for example, graft versus host disease.

Depending on the route of administration, the active ingredient may be required to be coated in a material to protect said ingredients from the action of enzymes, acids and other natural conditions which may inactivate said ingredient.

In order to administer the active ingredient by means other than parenteral administration, it will be coated by, or administered with, a material to prevent its inactivation. For example, the active ingredient may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water emulsions as well as conventional liposomes.

The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In certain cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient in the required amount in the appropriate solvent with several of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Various other materials may be present as coatings or to otherwise modify the physical form of the dosage unit. Of course, any material used in preparing any dosage unit form should be pharmaceutically pure and substantially non-toxic in the amounts employed. In addition, the active ingredient may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. In certain embodiments the pharmaceutically acceptable carrier or diluent is an aqueous fluid. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms described herein are dictated by and directly dependent on (a) the unique characteristics of the active material and the particular therapeutic effect to be achieved, and (b) the limitations inherent in the art of compounding such as active material for the treatment of disease in living subjects having a disease or condition in which bodily health is impaired. The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

Dosages may include, but are not limited to, 0.01 mg/kg to 20 mg/kg, including: 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.10 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11.0 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12.0 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13.0 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14.0 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15.0 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, 15.9 mg/kg, 16.0 mg/kg, 16.1 mg/kg, 16.2 mg/kg, 16.3 mg/kg, 16.4 mg/kg, 16.5 mg/kg, 16.6 mg/kg, 16.7 mg/kg, 16.8 mg/kg, 16.9 mg/kg, 17.0 mg/kg, 17.1 mg/kg, 17.2 mg/kg, 17.3 mg/kg, 17.4 mg/kg, 17.5 mg/kg, 17.6 mg/kg, 17.7 mg/kg, 17.8 mg/kg, 17.9 mg/kg, 18.0 mg/kg, 18.1 mg/kg, 18.2 mg/kg, 18.3 mg/kg, 18.4 mg/kg, 18.5 mg/kg, 18.6 mg/kg, 18.7 mg/kg, 18.8 mg/kg, 18.9 mg/kg, 19.0 mg/kg, 19.1 mg/kg, 19.2 mg/kg, 19.3 mg/kg, 19.4 mg/kg, 19.5 mg/kg, 19.6 mg/kg, 19.7 mg/kg, 19.8 mg/kg, 19.9 mg/kg, and 20.0 mg/kg.

Dosages may also include, but are not limited to: about 100 ng/kg to about 0.01 mg/kg, including: about 100 ng/kg, about 200 ng/kg, about 300 ng/kg, about 400 ng/kg, about 500 ng/kg, about 600 ng/kg, about 700 ng/kg, about 800 ng/kg, about 900 ng/kg, about 1 microgram/kg, about 2 microgram/kg, about 3 microgram/kg, about 4 microgram/kg, about 5 microgram/kg, about 6 microgram/kg, about 7 microgram/kg, about 8 microgram/kg, about 9 microgram/kg, about 10 microgram/kg.

In order to facilitate delivery of peptide compounds, including antibodies, to cells, peptides may be modified in order to improve their ability to cross a cell membrane. For example, U.S. Pat. No. 5,149,782 discloses the use of fusogenic peptides, ion-channel forming peptides, membrane peptides, long-chain fatty acids and other membrane blending agents to increase protein transport across the cell membrane. These and other methods are also described in WO 97/37016 and U.S. Pat. No. 5,108,921, incorporated herein by reference.

In a further aspect there is provided the active ingredient described herein for use in the treatment of disease either alone or in combination with art recognized compounds known to be suitable for treating the particular indication. Consequently, there is provided the use of an active ingredient described herein for the manufacture of a medicament for the treatment of disease associated with an aberrant immune response.

Moreover, there is provided a method for treating a condition associated with an aberrant immune response, comprising administering to a subject a therapeutically effective amount of a ligand identifiable using an assay method as described above.

The examples provided below are for the purposes of illustration only, and should not be considered limiting on the compositions and methods described herein.

EXAMPLES

Example 1: Accelerated Stability Study of VH31 Anti-αβTCR Antibody Formulations

An accelerated stability study was performed on various formulations of the VH31 antibody. The reference or control VH31 antibody is a wild-type humanized anti-human αβTCR antibody in the GL1BM series, comprising a heavy chain variable domain with the amino acid sequence set forth as SEQ ID NO: 16 and a light chain variable domain with the amino acid sequence set forth as SEQ ID NO: 14 (Table 1). No fragmentation was observed in liquid formulations after four months at refrigerated temperatures of 4° C. or less. However, fragments were detected in VH31 liquid formulations subjected to accelerated conditions that included increased temperature and pH (i.e., 45° C.; pH 4.0-8.0) for five weeks. It was noted that the presence of two low molecular weight (LMW) bands appeared to correlate with the disappearance of a band corresponding to the light chain (LC) of the VH31 antibody (FIG. 1, arrows), implicating light chain fragmentation of the source of the observed LMW species.

Example 2: Cell-Based Assay to Evaluate the Potency of the Stressed Formulations The VH31 anti-αβTCR antibody selectively depletes activated T cells. To determine whether VH31 formulations exposed to accelerated conditions retained this capability, a cell-based potency assay was performed. The potency assay is based on the activation of the T-cell receptor and the subsequent binding of the anti-αβTCR antibody to stimulate the apoptotic pathway.

Jurkat T lymphocytes express the T-cell receptor complex. The potency assay utilizes a Jurkat T-cell line containing a nuclear factor of activated T cells (NFAT) response element linked to a luciferase reporter. This engineered cell line is used to examine T-cell activation and subsequent inhibition of the activation signal by the anti-αβTCR antibody. Activation of the T-cell receptor complex stimulates the NFAT pathway leading to luciferase production. Luciferase production is then measured using luciferase substrate (e.g., luciferin) and a luminescence detector. The level of activation is proportional to luciferase production. Immobilized anti-CD3 activates the Jurkat T cells, as measured through induction of the NFAT pathway and subsequent luciferase production in the NFAT-luciferase Jurkat cells. Activation is inhibited in a dose dependent manner by the anti-αβTCR antibody, which is a qualitative measure of anti-αβTCR potency.

The qualitative potency assay was run in a 96-well plate format. The 96-well plates were coated with 1 μg/mL of anti-CD3 at 2-8° C. overnight. The plates were washed and NFAT-luciferase Jurkat T lymphocytes ($5\times10^4$ cells/well) were added to the anti-CD3-coated plates. The cells were incubated with anti-CD3 at 37° C. and 5% $CO_2$ for five hours, in order to activate the T-cell receptor complex. Each cell condition was then incubated with multiple levels (0.003 to 200 μg/mL) of anti-αβTCR (control and sample) for an additional eighteen hours. Negative anti-CD3 (0 μg/mL) and anti-αβTCR (0 μg/mL) controls were included for each condition. After the second incubation step, the anti-αβTCR dilutions were removed and the cells were lysed with cell culture lysis reagent. The lysates were measured for luciferase production using luciferase substrate and a luminescence plate reader. Higher doses of anti-αβTCR antibody are expected to result in a lower luminescent signal, indicating inhibition of the activation response. Dose response data were plotted using Softmax Pro software and sample dose response curves were visually compared to control dose response curves.

Figure 2:
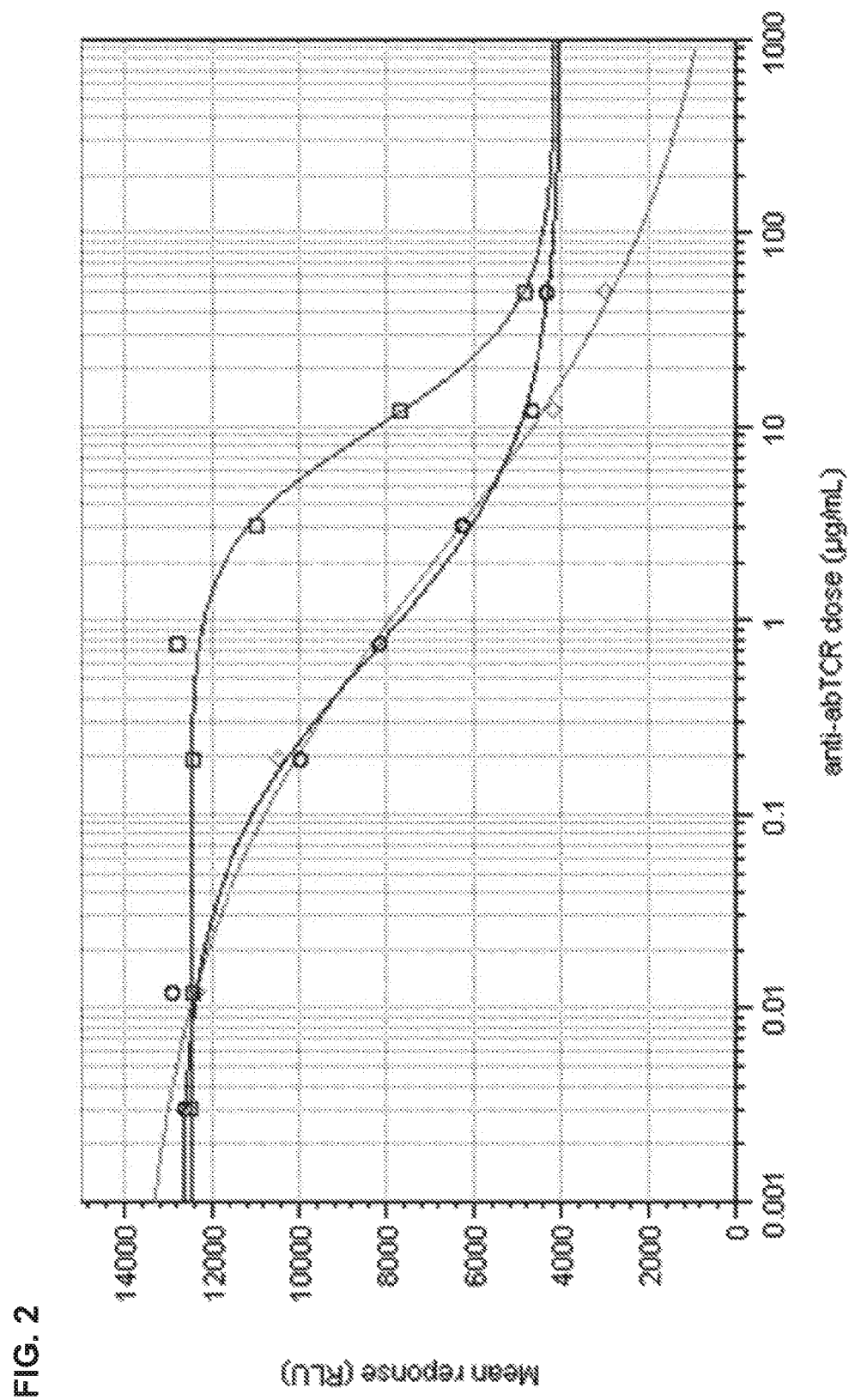
FIG. 2 is a line graph plotting the potency of the reference VH31 formulated antibody at varying concentrations under accelerated conditions for five weeks. The open squares correspond to the reference VH31 antibody stored at 45° C., pH 8.0; open circles correspond to the reference VH31 antibody stored at 45° C., pH 5.0; and open diamonds correspond to the reference VH31 antibody stored under control conditions, i.e., ≤0° C.; pH 5.0.

The graph in FIG. 2 shows data from the cell-based potency assay. The VH31 antibody formulation exposed to accelerated conditions (i.e., 45° C.; pH 8.0) for five weeks (open square symbols) showed considerable loss of potency compared to the VH31 formulation exposed to less severe conditions (i.e., 45° C.; pH 5.0) for five weeks (open circle symbols) or the control conditions (i.e., s 0° C.; pH 5.0; open diamond symbols). This study demonstrated a relationship between the appearance of the LMW species and a loss of antibody potency, likely due to light chain fragmentation.

Example 3: Analysis of Antibody Fragments

Figure 3:
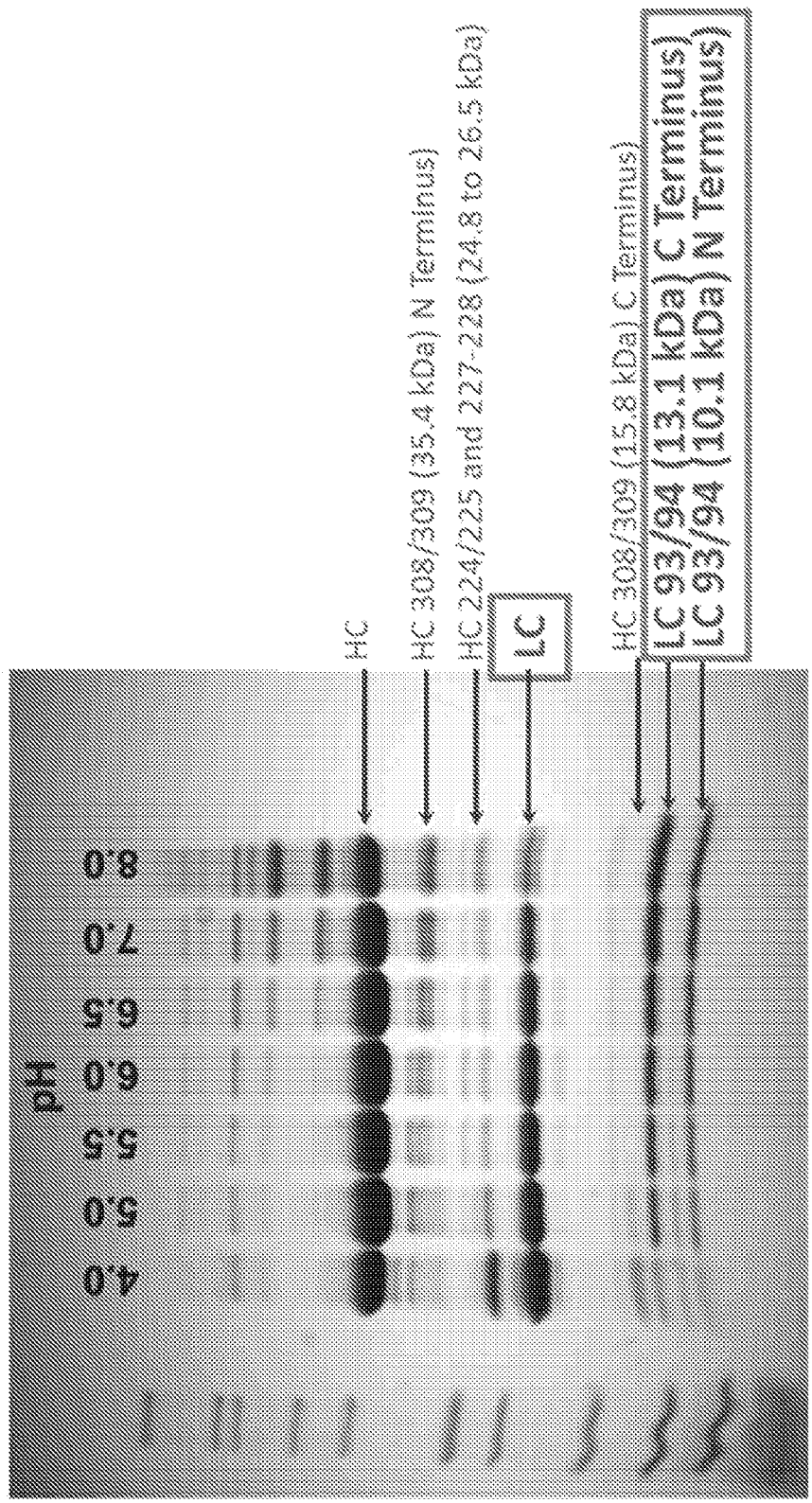
FIG. 3 is a photograph of a protein gel showing assigned identities, based on molecular weight and N-terminal sequencing, of the reference VH31 bands which were present under the indicated accelerated conditions. HC, heavy chain; LC, light chain.
Figure 4:
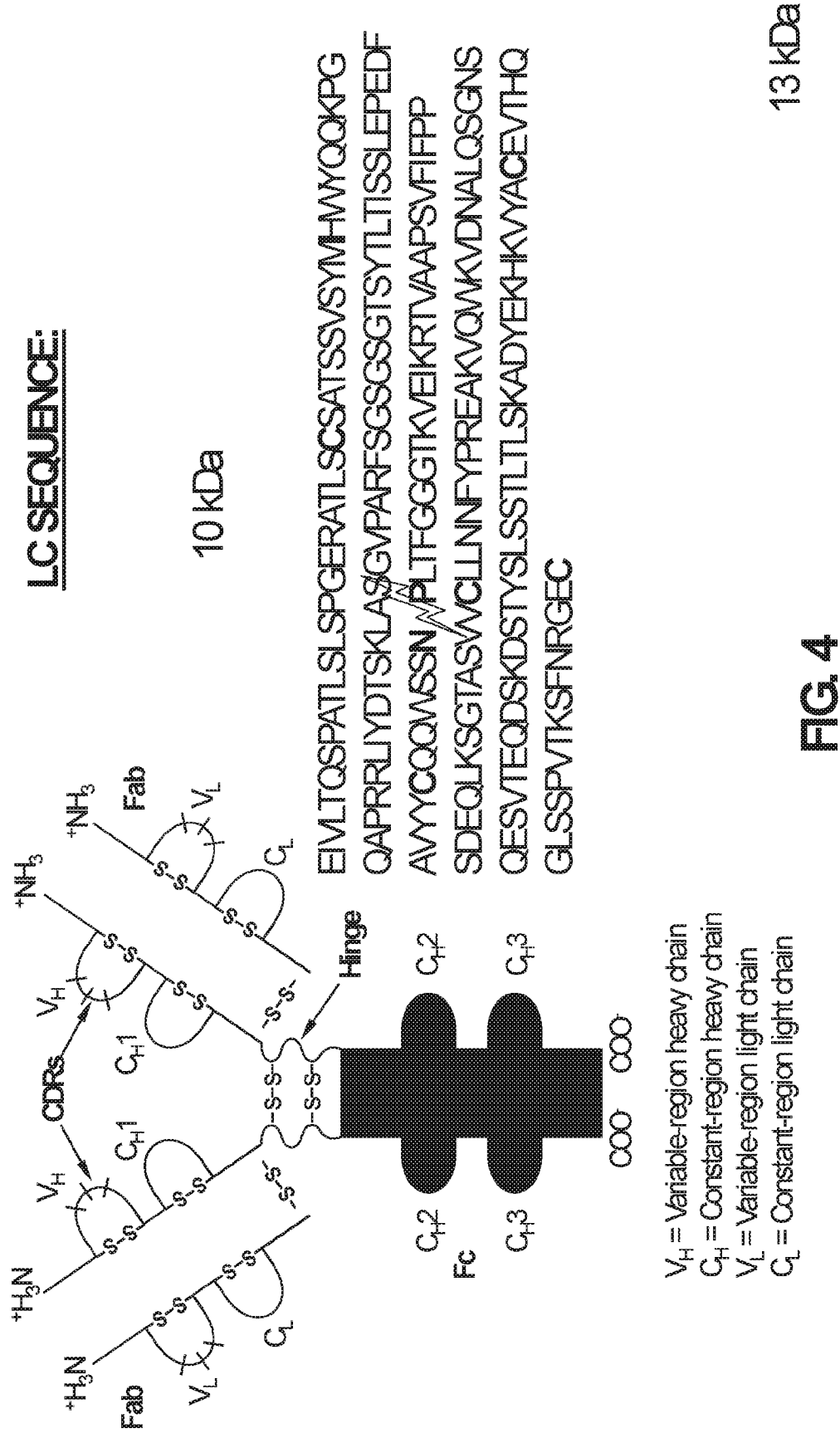
FIG. 4 depicts the reference VH31 light chain (LC) amino acid sequence (SEQ ID NO: 25) and the N93/P94 putative clipping site.
Figure 5A:
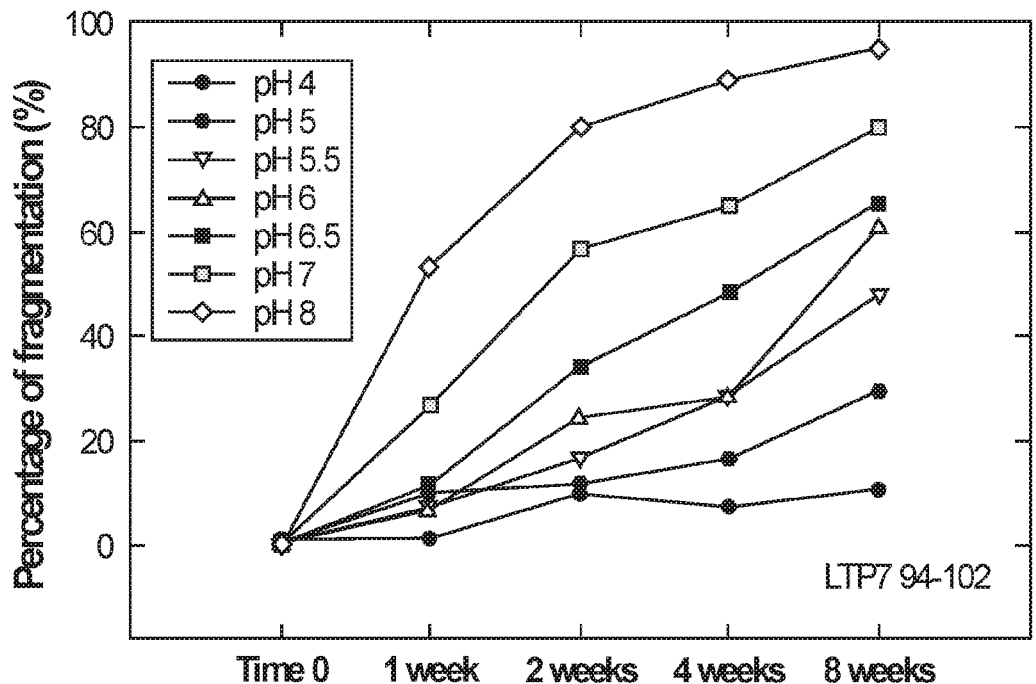
FIGS. 5A-5C are line graphs showing the various light chain fragments resulting from clipping at N93/P94 of trypsin digestion products (amino acids 61-102 or 61-106 according to Kabat numbering) of reference VH31 light chain. These fragments correspond to amino acid residues 94-102 (FIG. 5A), residues 61-93 (FIG. 5B), and residues 94-106 (FIG. 5C) of the VH31 LC. The 102 and 106 C-termini are due to incomplete tryptic digestion.
Figure 5B:
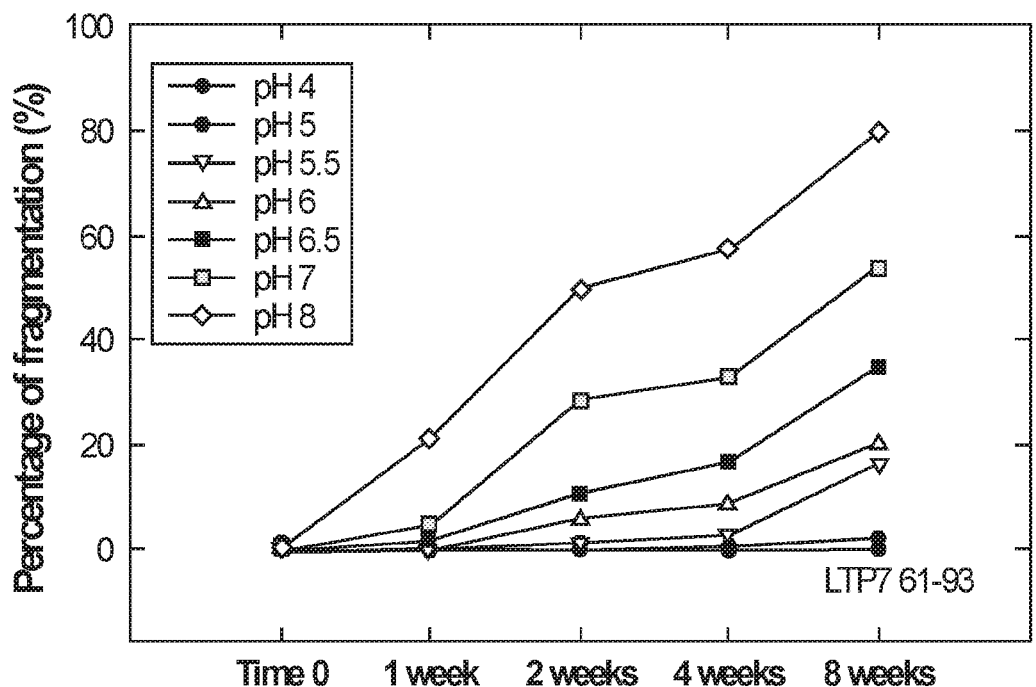
Figure 5C:
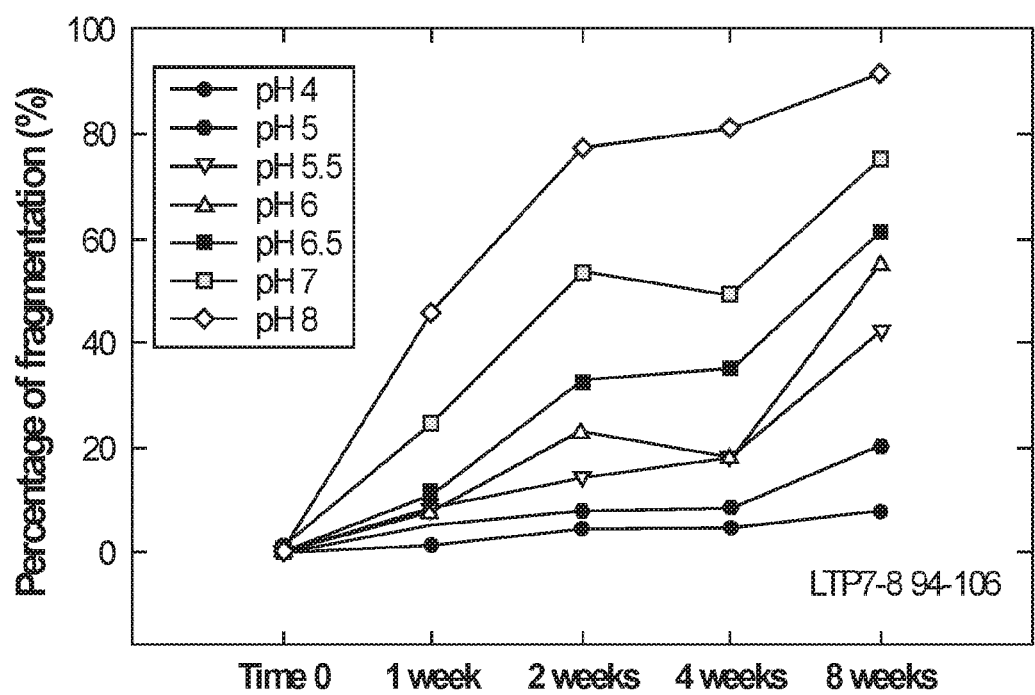

Antibody fragments were further analyzed by molecular weight estimation of the observed bands, as well as through N-terminal sequencing and peptide mapping studies (FIG. 3). Chemical and enzymatic cleavage of polypeptides is known to occur between Asn (N) and Pro (P) residues. Therefore, based on sequencing and mapping studies, light chain amino acid residues N93 and P94 were identified as the probable location of light chain clipping and the source of the identified fragments (FIG. 4). To further confirm this, the VH31 light chain (P7) was subjected to trypsin digestion at pH 4.0 to 8.0. The graphs in FIG. 5 show the various light chain fragments that were expected if enzymatic clipping were to occur at N93/P94. These fragments correspond to amino acid residues 94-102 (FIG. 5A), residues 61-93 (FIG. 5B), and residues 94-106 (FIG. 5C). The two C-terminal products corresponding to amino acids 94-102 and 94-106 are due to incomplete tryptic digestion. As expected, an increase in pH related to an increase in the predicted fragments.

Figure 6:
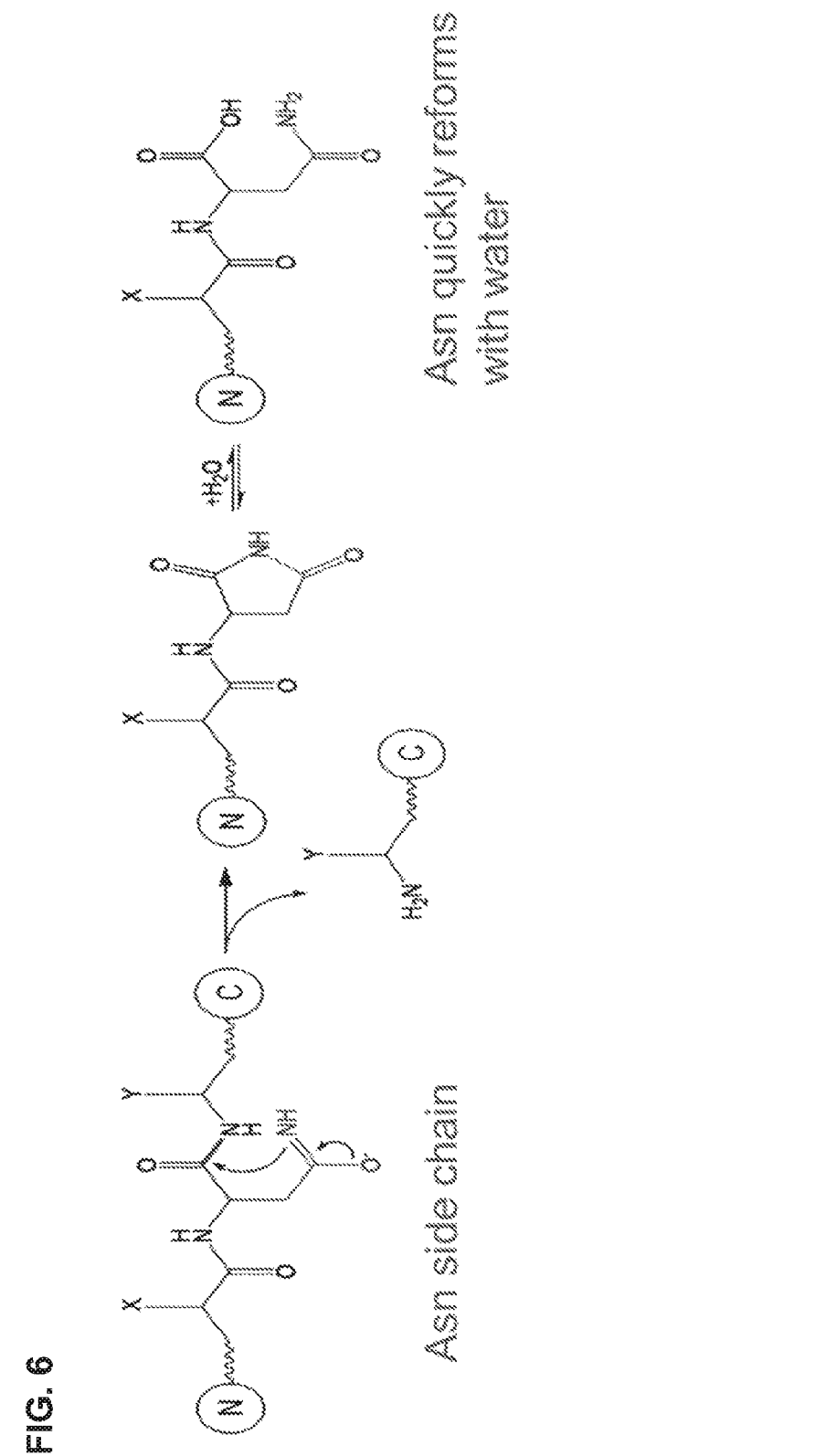
FIG. 6 depicts proposed process by which cleavage at Asn 93 (N93) may occur in solution.

It is known that Asn (N) may convert to Asp (D) in solution, e.g., through deamidation of the Asn side chain (FIG. 6). To better understand the mechanism of LC fragmentation, LC fragments were analyzed to determine whether residue 93 was N or D. Isotope distribution revealed that the majority of the 61-93 peptide fragments ended in Asn. No separate peak corresponding to D93 was observed, indicating that conversion of Asn to Asp, followed by Asp/Pro cleavage, was not the primary cause of VH31 LC fragmentation. For these reasons, subsequent engineered stability studies focused upon residues N93/P94.

Example 4: Engineering Light Chain (LC) Variants by Mutagenesis

A mutagenesis approach was taken to engineer VH31 light chain variants with increased stability and resistance to fragmentation. Previous attempts at removing Asn clipping sites in an unrelated antibody (i.e., sFLT01) did not prevent antibody fragmentation. Further complicating matters, it was noted that amino acid residues N93 and P94 reside within the light chain complementarity determining region 3 (LC CDR3). Considering the above, light chain variants were rationally designed with the goal of enhancing light chain stability while simultaneously retaining antigen binding affinity and antibody potency.

The amino acid Pro (P) provides little freedom in folded protein structures. Therefore, it was postulated that it may be difficult to replace Pro at residue 94 without destabilizing the conformation of the LC CDR3. Ala (A) is commonly used in mutagenesis due to its physical characteristics. As a starting point, residues N93 and P94 were either individually or concomitantly replaced with A. In addition, several other substitutions were made at residue N93, based on amino acid characteristics that were thought to be compatible, e.g., charge, size, H-bonding, polar vs. non-polar, etc. FIG. 7 shows the various amino acid substitutions that were made and tested.

Wild-type anti-αβTCR VH31 expression vector was used as the template for mutagenesis and expression control. Eight pairs of primers were designed, and PCR mutagenesis was performed using the QuikChange Lightning Site-Directed Mutagenesis Kit (Agilent). Mutant DNAs were then confirmed by DNA sequencing.

Example 5: Expression and Analysis of LC Variants

Mutant and wild-type (WT) DNA were transfected into the Expi293 transient expression system. Conditioned media were harvested four days post-transfection, and expression levels were measured by Octet Protein A assay. The results (shown in Table 2) indicated good expression for the αβTCR wild-type (114 µg/mL media) and 7 of the 8 mutants (>45 µg/mL media). One mutant (N93A) was expressed at a relatively lower level (16 µg/mL). The transfection was scaled up to 30 mL for all 8 mutants. Conditioned media were collected for Protein A purification.

The conditioned media were put through the 1 mL HiTrap Protein A HP (GE) column for purification. The column was equilibrated with PBS pH 7.2 (Gibco) for 5 column volumes. The media were loaded at a 0.5 mL/min flow rate and then washed with PBS pH 7.2 for 20 column volumes (CVs) before elution. Antibody was eluted into 10 mM succinate, pH 3.75 and adjusted to pH 5.5 with 0.2 M sodium hydroxide right after elution. All samples were filtered with 0.2 µm low-protein binding membrane with a syringe filter (recovery 50%-80%) and Amicon YM30 was used to concentrate the sample (recovery 100%). The results are summarized in Table 2.

TABLE 2

| ID | Sample | Expression level (µg/mL media) | After purification (µg/mL) | Volume (mL) | Total Purified (µg) |
|---|---|---|---|---|---|
| WT | αβTCR WT | 114 | 341 | 2 | 682 |
| 1 | αβTCR N93Q | 33.7 | 355 | 0.98 | 348 |
| 2 | αβTCR N93D | 30.2 | 350 | 0.98 | 343 |
| 3 | αβTCR N93H | 38.1 | 394 | 0.92 | 362 |
| 4 | αβTCR N93S | 42.6 | 250 | 1.94 | 485 |
| 5 | αβTCR N93Y | 9.7 | 316 | 0.255 | 81 |
| 6 | αβTCR N93A | 33.7 | 370 | 1 | 370 |
| 7 | αβTCR P94A | 29.2 | 339 | 0.92 | 312 |
| 8 | N93A P94A | 30 | 267 | 1.94 | 518 |

Figure 8:
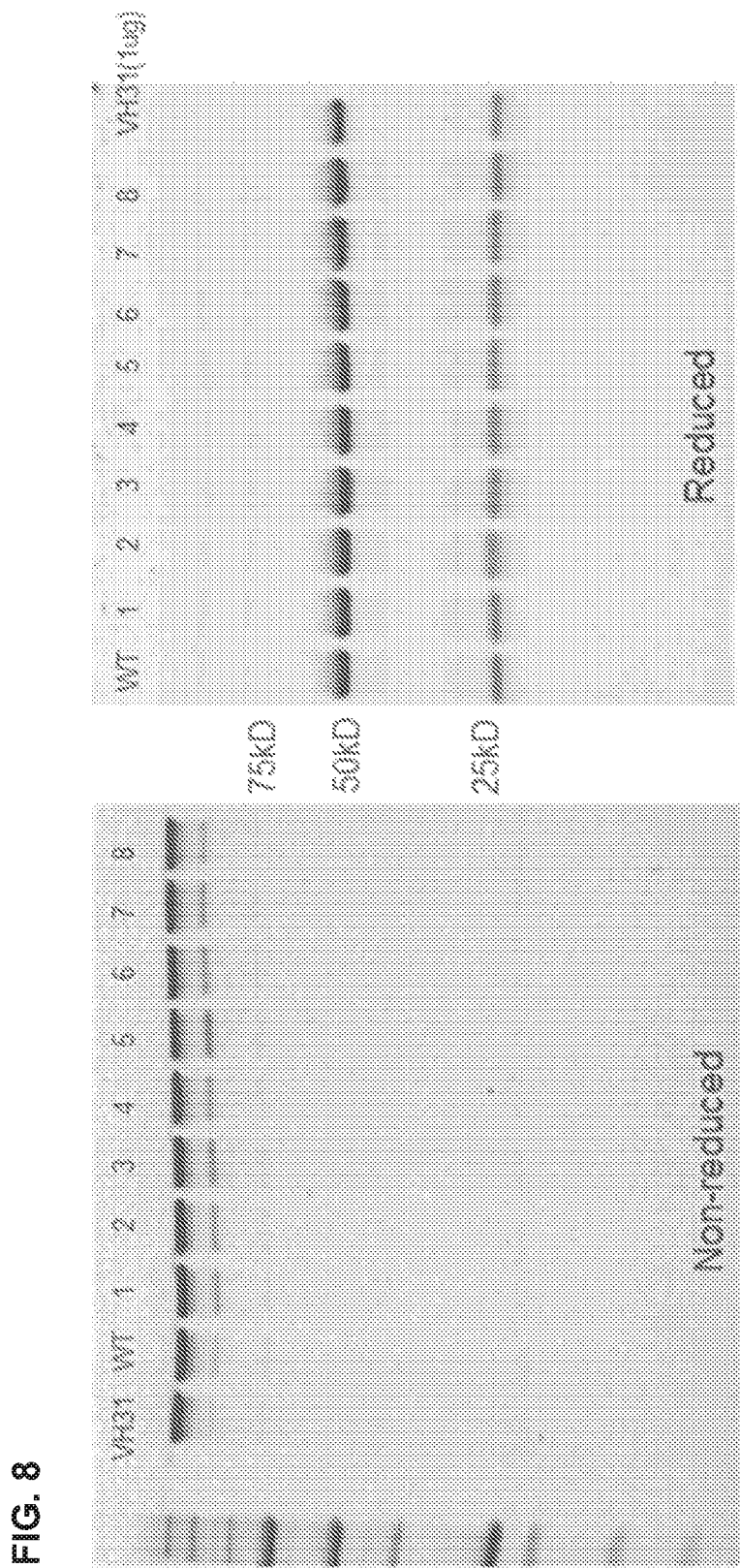
FIG. 8 is a pair of photographs of protein gels showing the high expression and purity of VH31 antibodies containing either a mutated (lanes 1-8) or a non-mutated LC. 1, N93Q; 2, N93D; 3, N93H; 4, N93S; 5, N93Y; 6, N93A; 8, N93A/P94A.

Purified antibodies were run on Mini-PROTEAN TGX Stain-Free Gels (Bio-Rad), 1.5 µg load per well. The result showed that the all mutants tested were comparable to WT and had good purity (FIG. 8). Purified mutants were subjected to further characterization by stability and functional assays.

Sixty milliliter-scale transfections of αβTCR N93S mutant was performed in the Expi293 transient expression system. Conditioned media were harvested four days post-transfection. The expression levels were measured by Octet Protein A assay and determined to be 37 µg/mL.

Figure 9:
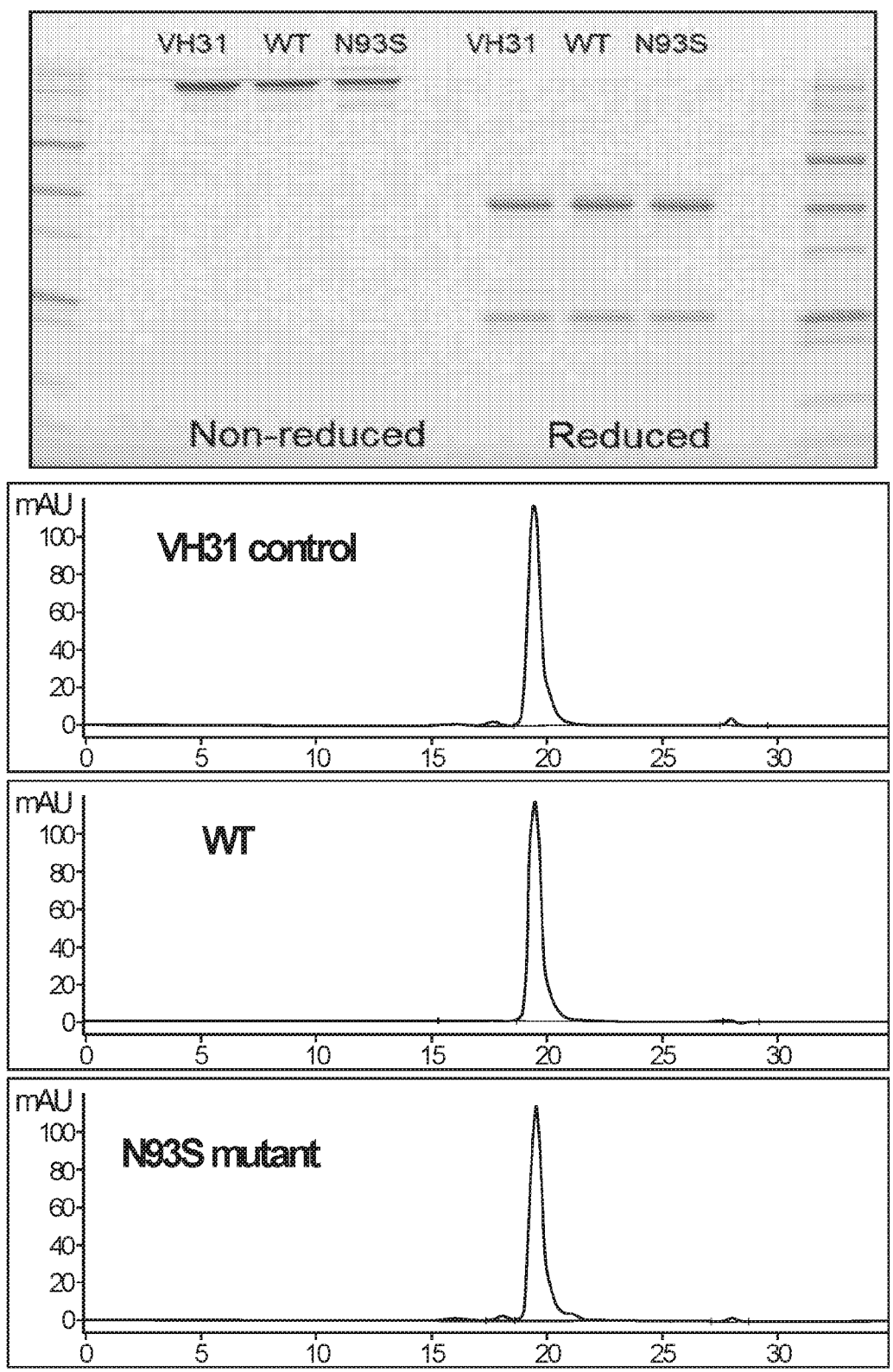
FIG. 9 is a photograph of a pair of protein gels (left panel) and three SEC-HPLC plots (right panel) showing that the purity of an antibody comprising a N93S LC mutation was comparable to wildtype (WT) and control (VH31) antibodies.

HiTrap Protein A HP (GE) column (1 mL) was used for purification. The column was equilibrated with PBS pH 7.2 (Gibco) for 5 CVs. Conditioned media sample was loaded at 0.5 mL/min flow rate and then washed with PBS pH 7.2 for 20 CVs before elution. Antibody was eluted into 10 mM succinate, pH 3.75 for 5 CVs (5 mL in total) and the yield was almost 100%. Eluted antibody was adjusted to pH 5.5 with 0.2 M sodium hydroxide after elution. Solutions turned slightly cloudy at pH 5.5 and were filtered with 50 mL tube top filters (0.2 µm CA, low protein binding). Filtration recovery was 77% (1.7 mg total), possibly due to the relatively large volume loss. Purified antibodies and the αβTCR VH31 control were run on Mini-PROTEAN TGX Stain-Free Gels (2 µg load per well). The result showed that all mutants tested were comparable to the VH31 control. Purified N93S and previously purified WT and VH31 control were run on SEC-HPLC and the profile is shown in FIG. 9. SEC profile of both WT and N93S mutant appeared to be comparable to VH31 control.

Example 6: Assay to Evaluate the Potency of LC Variants

Figure 10:
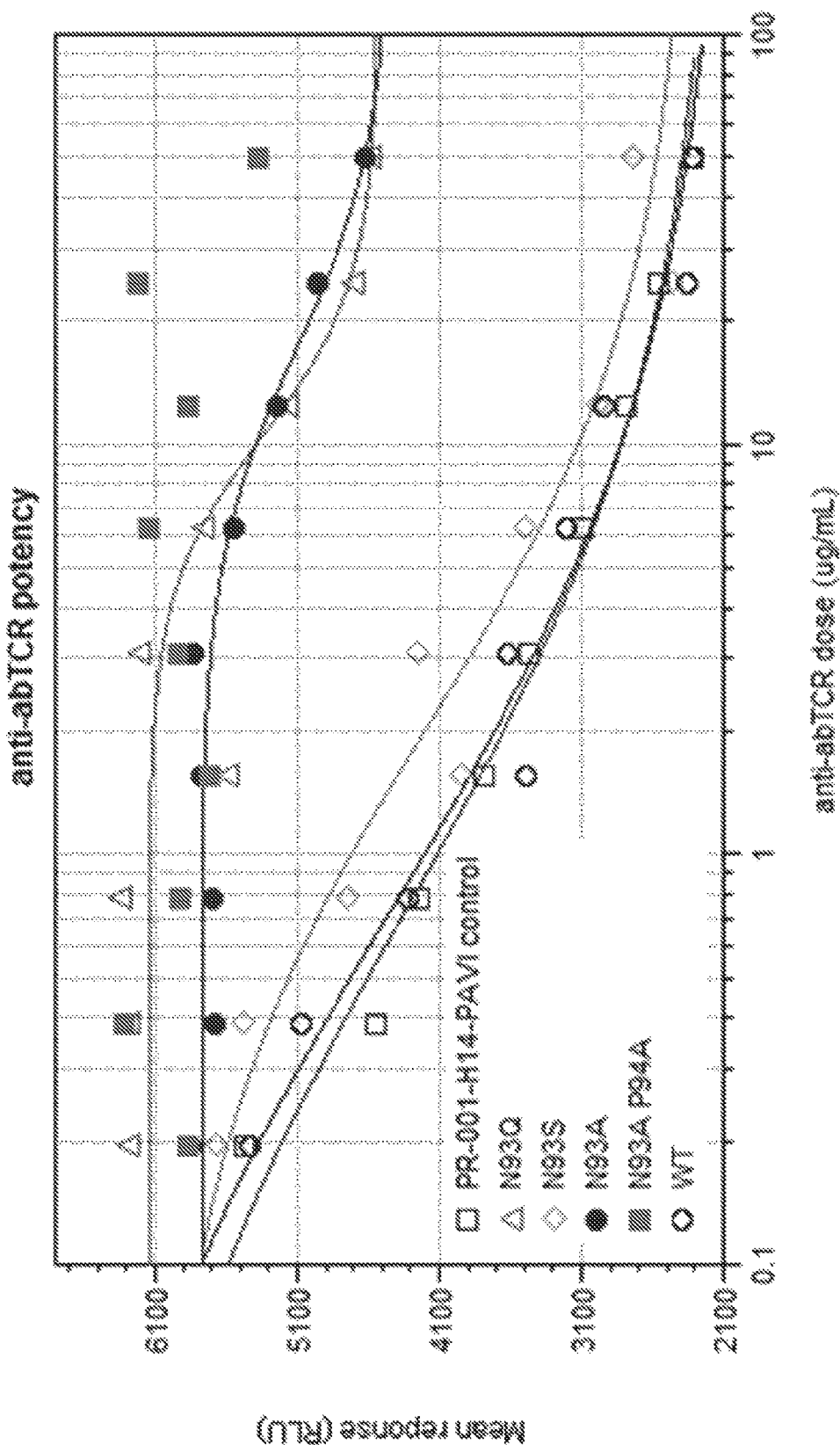
FIG. 10 is a line graph plotting the potency of VH31 antibodies comprising the indicated LC mutations. An antibody comprising LC variant N93S (open diamond symbols) was only slightly less potent than either the reference VH31 (open square symbols) or wildtype (WT) antibody (open octagon symbols).

The qualitative potency assay described in Example 2 was repeated with antibodies comprising the variant light chains. The wildtype and control antibodies comprised the identical VH31 amino acid sequence, but were produced from different preparations. The wildtype VH31 antibody was produced together with the LC variant antibodies, whereas the control antibody was produced from a separate large-scale preparation. As shown in FIG. 10, an antibody comprising LC variant N93S was only slightly less potent than either the wildtype VH31 or control antibody. In contrast, antibodies comprising LC variants N93Q, N93A, and N93A/P94A were all markedly less potent than any of the aforementioned antibodies. Based on these results, the N93S variant was selected as a candidate for accelerated stability studies.

Example 7: Accelerated Stability Studies of LC Variants

Figure 11:
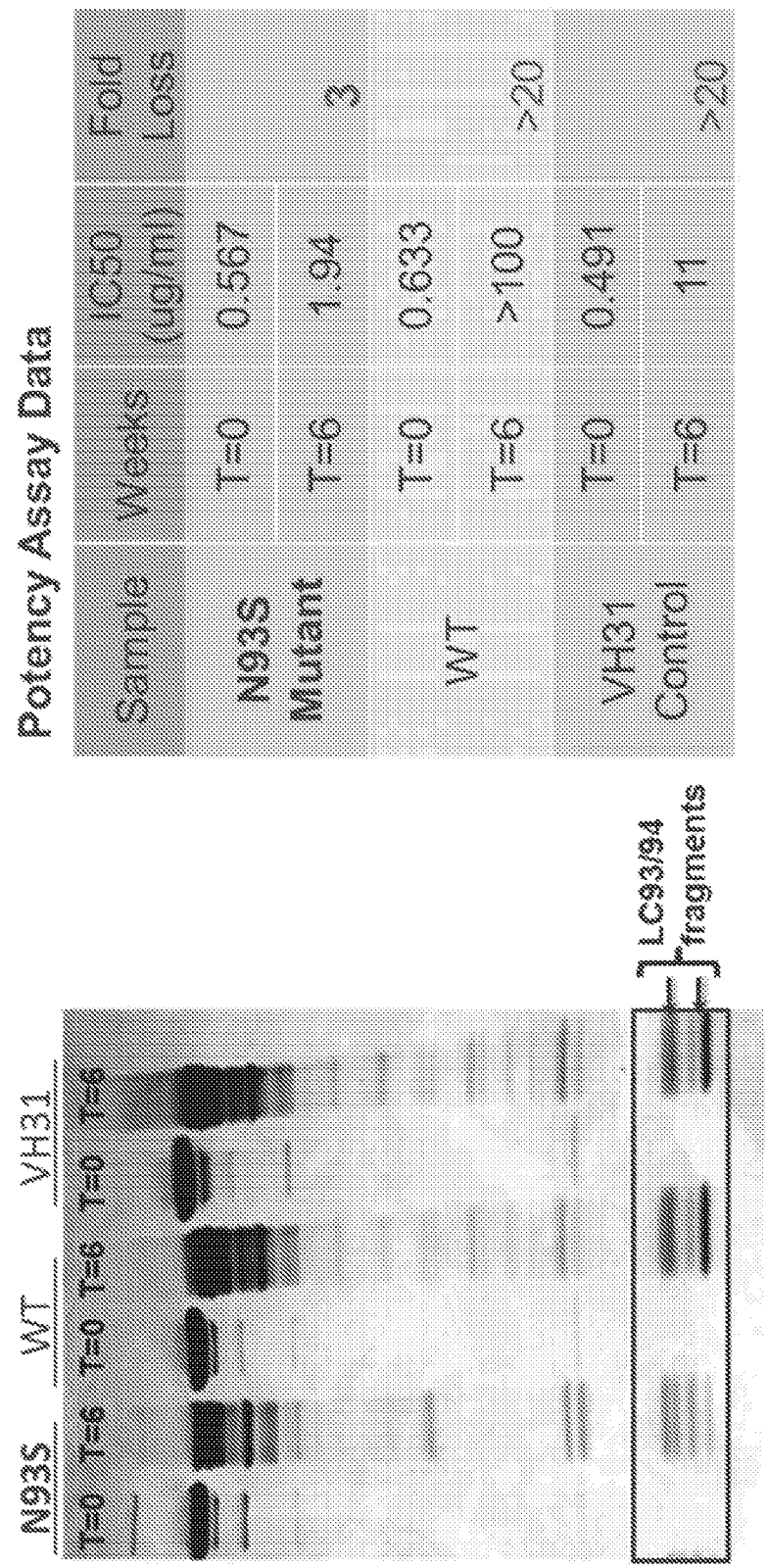
FIG. 11 is a photograph of a protein gel showing (left panel) that the N93S mutant had demonstrably reduced degradation compared to either the wildtype (WT) or the VH31 control antibody upon 6 weeks storage at 45° C., pH 8. The right panel shows that the N93S mutant had markedly less loss of potency under accelerated conditions (3-fold loss) compared to either the wildtype or VH31 control antibodies (each greater than 20-fold loss).
Figure 12:
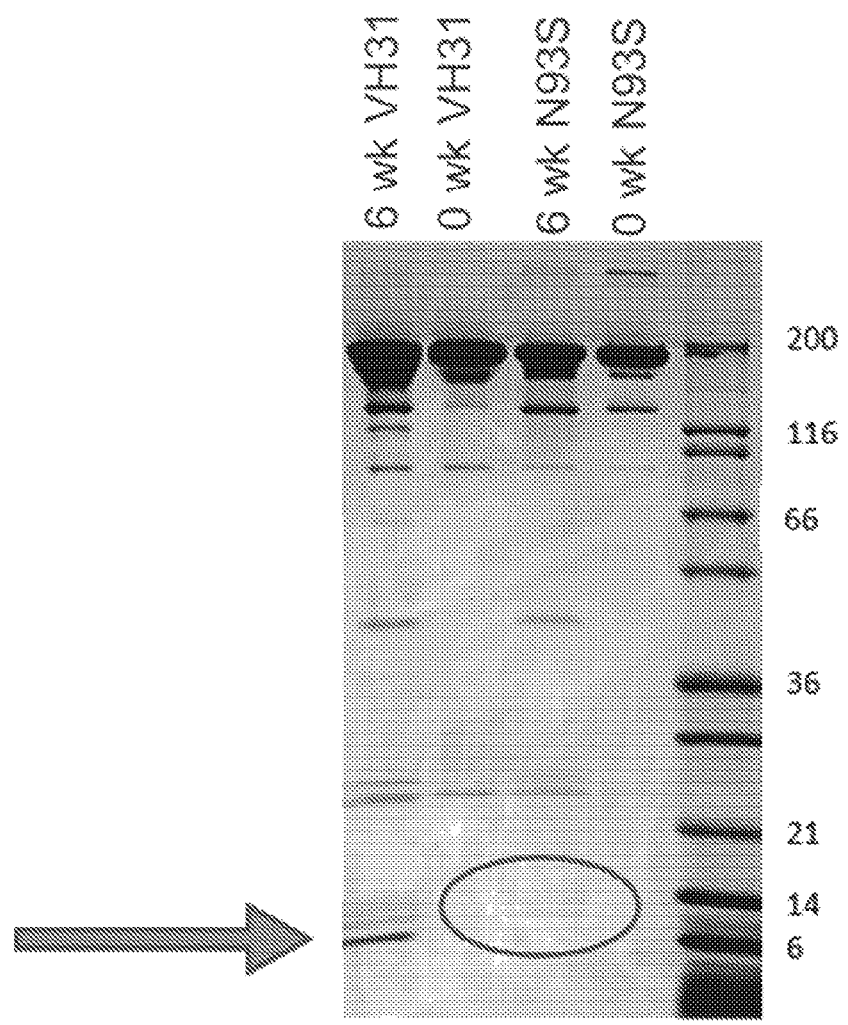
FIG. 12 is a photograph of a protein gel showing fragmentation of the reference VH31 antibody and the N93S mutant following storage for six weeks at elevated temperature (45° C.) at pH 5.5.

The antibody comprising the LC variant N93S was subjected to increased temperature (i.e., 45° C.) and pH (i.e., pH 8.0) for six weeks to determine whether the N93S amino acid substitution stabilized the LC and prevented fragmentation. After six weeks at elevated temperature and pH 8.0, fragmentation was observed in wildtype, reference VH31, and N93S antibodies. However, the N93S mutant had demonstrably reduced degradation compared to either the wildtype or VH31 control antibodies (FIG. 11). Notably, the N93S mutant had markedly reduced loss of potency under accelerated conditions (3-fold loss) compared to either the wildtype or VH31 control antibodies (each greater than 20-fold loss). At pH 5.5, which is closer to the pH of a hypothetical antibody drug substance formulation than pH 8.0, fragmentation was noticeably less prevalent at six weeks (FIG. 12).

The aforementioned results showed that, compared to the VH31 αβTCR antibody, the N93S mutant demonstrated improved LC stability and potency under storage conditions, including under increased temperature and elevated pH. These results are surprising because previous attempts at removing Asn clipping sites in an unrelated antibody (i.e., sFLT01) did not prevent antibody fragmentation.

What is claimed is:

1. A binding polypeptide that specifically binds human αβTCR/CD3 complex, comprising a heavy chain variable region, a light chain variable region, and a constant region, wherein:
   the light chain variable region comprises three complementarity determining regions (CDRs) LCDR1, LCDR2, and LCDR3 comprising the amino acid sequences set forth in SEQ ID NOs: 26, 27, and 28, respectively;
   SEQ ID NO: 28 comprises the amino acid sequence Q-Q-W-S-S-$X_1$-$X_2$-L-T, wherein $X_1$ is an amino acid selected from the group consisting of Q, D, H, S, Y, and A, and $X_2$ is an amino acid selected from the group consisting of P and A;
   wherein the light chain variable region further comprises a human light chain framework region set forth in SEQ ID NO: 14;
   wherein the heavy chain variable region comprises any one of an amino acid sequence selected from the group consisting of SEQ ID NOs: 7, 12, 13, 15, and 16; and the constant region is of human origin.

2. The binding polypeptide of claim 1, wherein $X_1$ is S.

3. The binding polypeptide of claim 1, wherein $X_2$ is P.

4. The binding polypeptide of claim 1, wherein the heavy chain variable region comprises the sequences set forth in SEQ ID NO: 16.

5. The binding polypeptide of claim 1, wherein the binding polypeptide has increased stability at pH greater than 5.0 compared to a humanized anti-αβTCR antibody, VH31.

6. The binding polypeptide of claim 1, wherein the binding polypeptide has increased stability at a temperature greater than 4° C. compared to a humanized anti-αβTCR antibody, VH31.

7. The binding polypeptide of claim 1, wherein the constant region comprises an Fc modification with a modified glycosylation pattern that reduces Fcγ receptor binding, optionally wherein the Fcγ receptor is selected from the group consisting of FcγRIIIa and FcγRI.

8. The binding polypeptide of claim 7, wherein the Fc modification is selected from the group consisting of N297Q/S298N/Y300S, S298N/T299A/Y300S, and S298N/Y300S.

9. The binding polypeptide of claim 1, wherein the binding polypeptide is humanized.

10. The binding polypeptide of claim 1, wherein the binding polypeptide is a monoclonal antibody.

11. The binding polypeptide of claim 1, wherein the binding polypeptide is multispecific, optionally wherein the binding polypeptide is bispecific.

12. A pharmaceutical composition, comprising the binding polypeptide of claim 1 and a pharmaceutically acceptable carrier or diluent.

13. A formulation comprising the pharmaceutical composition of claim 12, wherein the formulation is selected from the group consisting of a lyophilized formulation and a liquid formulation.

14. A nucleic acid encoding the binding polypeptide according to claim 1.

15. A vector comprising the nucleic acid according to claim 14.

16. A cell which expresses the nucleic acid according to claim 14.

17. The cell according to claim 16, wherein the cell is a mammalian cell, optionally wherein the mammalian cell is selected from the group consisting of a Chinese hamster ovary (CHO) cell and a human embryonic kidney (HEK) cell.

18. A method of treating a subject for a T-cell-mediated disease or disorder, wherein the T cell mediated disease, or disorder arises due to transplantation of a cell, tissue, body part, or organ comprising administering to the subject an effective amount of the binding polypeptide of claim 1.

19. A method of treating a subject for a T-cell-mediated disease or disorder, wherein the T cell mediated disease, or disorder arises due to an autoimmune disease comprising administering to the subject an effective amount of the binding polypeptide of claim 1.

20. A method of treating a subject for a T-cell-mediated disease or disorder, wherein the T cell mediated disease, or disorder is multiple sclerosis comprising administering to the subject an effective amount of the binding polypeptide of claim 1.

21. A method of treating a subject for a T-cell-mediated disease or disorder, wherein the T cell mediated disease, or disorder is type I diabetes comprising administering to the subject an effective amount of the binding polypeptide of claim 1.

* * * * *

SEQUENCE LISTING

<160> NUMBER OF SEQ ID NOS: 29

<210> SEQ ID NO 1
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Thr Lys Tyr Asn Glu Lys Phe
50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ala
            115                 120

<210> SEQ ID NO 2
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 3
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
50                  55                  60

```
Lys Gly Lys Ala Thr Leu Thr Ala Asp Glu Ser Thr Asn Thr Ala Tyr
 65                  70                  75                  80

Met Glu Leu Ser Ser Leu Arg Ser Glu Asp Thr Ala Val His Tyr Cys
                 85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120
```

<210> SEQ ID NO 4
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 4

```
Asp Ile Gln Met Thr Gln Ser Pro Ser Thr Leu Ser Ala Ser Val Gly
  1               5                  10                  15

Asp Arg Val Thr Met Thr Cys Ser Ala Thr Ser Ser Val Ser Tyr Met
                 20                  25                  30

His Trp Tyr Gln Gln Lys Pro Gly Lys Ala Pro Lys Arg Trp Ile Tyr
             35                  40                  45

Asp Thr Ser Lys Leu Ala Ser Gly Val Pro Ala Arg Phe Ile Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 5
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 5

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Tyr Lys Phe Thr Ser Tyr
                 20                  25                  30

Val Met His Trp Val Lys Gln Ala Pro Gly Lys Gly Leu Glu Trp Ile
             35                  40                  45

Gly Tyr Ile Asn Pro Tyr Asn Asp Val Thr Lys Tyr Asn Glu Lys Phe
 50                  55                  60

Lys Gly Lys Ala Thr Leu Ser Arg Asp Asn Ser Lys Asn Thr Leu Tyr
 65                  70                  75                  80

Leu Gln Met Asn Ser Leu Arg Ala Glu Asp Thr Ala Val His Tyr Cys
                 85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120
```

<210> SEQ ID NO 6
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 6

```
Asp Ile Gln Met Thr Gln Ser Pro Ser Thr Leu Ser Ala Ser Val Gly
1               5                   10                  15
Asp Arg Val Thr Met Thr Cys Ser Ala Thr Ser Ser Val Ser Tyr Met
            20                  25                  30
His Trp Tyr Gln Gln Lys Pro Gly Lys Ala Pro Lys Arg Trp Ile Tyr
        35                  40                  45
Asp Thr Ser Lys Leu Ala Ser Gly Val Pro Ala Arg Phe Ile Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Gln Gln Trp Ser Ser Asn Pro Leu Thr
                85                  90                  95
Phe Gly Gly Gly Thr Lys Val Glu Ile Lys
            100                 105
```

<210> SEQ ID NO 7
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 7

```
Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Lys Phe Thr Ser Tyr
            20                  25                  30
Val Met His Trp Val Lys Gln Ala Pro Gly Lys Gly Leu Glu Trp Ile
        35                  40                  45
Gly Tyr Ile Asn Pro Tyr Asn Asp Val Thr Lys Tyr Asn Glu Lys Phe
    50                  55                  60
Lys Gly Lys Ala Thr Leu Ser Arg Asp Asn Ser Lys Asn Thr Leu Tyr
65                  70                  75                  80
Leu Gln Met Asn Ser Leu Arg Ala Glu Asp Thr Ala Val His Tyr Cys
                85                  90                  95
Ala Arg Gly Ser Tyr Tyr Asp Tyr Asp Gly Phe Val Tyr Trp Gly Gln
            100                 105                 110
Gly Thr Leu Val Thr Val Ser Ser
        115                 120
```

<210> SEQ ID NO 8
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 8

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Lys Phe Thr Ser Tyr
            20                  25                  30
```

Val Met His Trp Val Arg Gln Ala Pro Gly Gln Arg Leu Glu Trp Met
         35                  40                  45

Gly Tyr Ile Asn Pro Tyr Asn Asp Val Thr Lys Tyr Asn Glu Lys Phe
     50                  55                  60

Lys Gly Lys Ala Thr Ile Thr Arg Asp Thr Ser Ala Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 9
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 9

Glu Ile Val Leu Thr Gln Ser Pro Ala Thr Leu Ser Leu Ser Pro Gly
 1               5                  10                  15

Glu Arg Ala Thr Leu Ser Cys Ser Ala Thr Ser Ser Val Ser Tyr Met
                 20                  25                  30

His Trp Tyr Gln Gln Lys Pro Gly Gln Ala Pro Arg Arg Trp Ile Tyr
             35                  40                  45

Asp Thr Ser Lys Leu Ala Ser Gly Val Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 10
<211> LENGTH: 329
<212> TYPE: PRT
<213> ORGANISM: Artificial sequence
<220> FEATURE:
<223> OTHER INFORMATION: Synthetic polypeptide

<400> SEQUENCE: 10

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys

```
                    100                 105                 110
Pro Ala Pro Pro Val Ala Gly Pro Ser Val Phe Leu Phe Pro Pro Lys
                115                 120                 125
Pro Lys Asp Thr Leu Met Ile Ser Arg Thr Pro Glu Val Thr Cys Val
            130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Gly Leu Pro Ser Ser Ile Glu Lys Thr Ile Ser Lys Ala Lys Gly Gln
    210                 215                 220
Pro Arg Glu Pro Gln Val Tyr Thr Leu Pro Pro Ser Arg Asp Glu Leu
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 11
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 11

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
```

```
                130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 12

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 13
<211> LENGTH: 120
<212> TYPE: PRT
<213> ORGANISM: Artificial sequence
<220> FEATURE:
<223> OTHER INFORMATION: Synthetic polypeptide
```

<400> SEQUENCE: 13

Glu Val Gln Leu Leu Glu Ser Gly Gly Gly Leu Val Gln Pro Gly Gly
1               5                   10                  15

Ser Val Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 14
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 15
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

```
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 16
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
                 20                  25                  30

Val Met His Trp Val Arg Gln Ala Pro Gly Gln Gly Leu Glu Trp Ile
             35                  40                  45

Gly Tyr Ile Asn Pro Tyr Asn Asp Val Thr Lys Tyr Asn Glu Lys Phe
     50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 17
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 18
```

```
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 19
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 20
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Val Met His Trp Val Arg Gln Ala Pro Gly Gln Arg Leu Glu Trp Met
            35                  40                  45

Gly Tyr Ile Asn Pro Tyr Asn Asp Val Thr Lys Tyr Asn Glu Lys Phe
        50                  55                  60

Lys Gly Lys Ala Thr Ile Thr Arg Asp Thr Ser Ala Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 21
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Tyr Gln Gln Lys Pro Gly Gln Ala Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
                100                 105

<210> SEQ ID NO 22
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Tyr Gln Gln Lys Pro Gly Gln Ala Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Phe Thr Leu Thr Ile Ser Ser Met Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
                100                 105

<210> SEQ ID NO 23
<211> LENGTH: 120
<212> TYPE: PRT
<213> ORGANISM: Artificial sequence
<220> FEATURE:
```

<223> OTHER INFORMATION: Synthetic polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 25
<211> LENGTH: 213
<212> TYPE: PRT
<213> ORGANISM: Artificial sequence
<220> FEATURE:
<223> OTHER INFORMATION: Synthetic polypeptide

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Leu Ile Tyr

```
                35                  40                  45
Asp Thr Ser Lys Leu Ala Ser Gly Val Pro Ala Arg Phe Ser Gly Ser
 50                  55                  60

Gly Ser Gly Thr Ser Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 26
<211> LENGTH: 10
<212> TYPE: PRT
<213> ORGANISM: Artificial sequence
<220> FEATURE:
<223> OTHER INFORMATION: Synthetic peptide

<400> SEQUENCE: 26

```
Ser Ala Thr Ser Ser Val Ser Tyr Met His
 1               5                  10
```

<210> SEQ ID NO 27
<211> LENGTH: 7
<212> TYPE: PRT
<213> ORGANISM: Artificial sequence
<220> FEATURE:
<223> OTHER INFORMATION: Synthetic peptide

<400> SEQUENCE: 27

```
Asp Thr Ser Lys Leu Ala Ser
 1               5
```

<210> SEQ ID NO 28
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Gln, Asp, His, Ser, Tyr, or Ala
<220> FEATURE:
<221> NAME/KEY: MISC_FEATURE
<222> LOCATION: (7)..(7)
<223> OTHER INFORMATION: Pro or Ala

<400> SEQUENCE: 28

```
Gln Gln Trp Ser Ser Xaa Xaa Leu Thr
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Gln Gln Trp Ser Ser Asn Pro Leu Thr
1               5
```